United States Patent
Smit et al.

(10) Patent No.: US 11,517,226 B2
(45) Date of Patent: Dec. 6, 2022

(54) OXYGEN SATURATION MONITORING USING ARTIFICIAL INTELLIGENCE

(71) Applicant: Covidien LP, Mansfield, MA (US)

(72) Inventors: Philip C. Smit, Hamilton (GB); Andre Antunes, Edinburgh (GB); Dean Montgomery, Edinburgh (GB); Paul S. Addison, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 246 days.

(21) Appl. No.: 17/061,344

(22) Filed: Oct. 1, 2020

(65) Prior Publication Data

US 2022/0104737 A1 Apr. 7, 2022

(51) Int. Cl.
*A61B 5/1455* (2006.01)
*A61B 5/00* (2006.01)

(52) U.S. Cl.
CPC ........ *A61B 5/14551* (2013.01); *A61B 5/7267* (2013.01); *A61B 5/7275* (2013.01); *A61B 5/742* (2013.01)

(58) Field of Classification Search
CPC . A61B 5/1455; A61B 5/14551; A61B 5/7267; A61B 5/7275
See application file for complete search history.

(56) References Cited

U.S. PATENT DOCUMENTS

| | | | |
|---|---|---|---|
| 5,865,736 A * | 2/1999 | Baker, Jr. | A61B 5/746 600/323 |
| 8,792,949 B2 * | 7/2014 | Baker, Jr. | A61B 5/7221 600/323 |
| 9,398,884 B2 * | 7/2016 | Tanishima | A61B 5/1455 |
| 9,861,317 B2 | 1/2018 | Ochs | |
| 2008/0183058 A1 | 7/2008 | Mannheimer | |
| 2014/0128696 A1 | 5/2014 | Al-Ali | |

(Continued)

OTHER PUBLICATIONS

Elmoaqet et al., "Evaluating Predictions of Critical Oxygen Desaturation Events," Physiological Measurement, Institute of Physics Publishing, Britsol, GB, vol. 35, No. 4, Mar. 12, 2014, pp. 639-655, XP020260242, ISSN: 0967-3334, DOI: 10.1088/0967-334/35/4/639.

(Continued)

*Primary Examiner* — Eric F Winakur
(74) *Attorney, Agent, or Firm* — Shumaker & Sieffert, P.A.

(57) ABSTRACT

In some examples, a system includes an oxygen saturation sensing device configured to sense an oxygen saturation level of a patient and processing circuitry. The processing circuitry may be configured to receive a signal indicative of the oxygen saturation level of the patient, determine that the signal indicates the oxygen saturation level is at or below a desaturation threshold, and in response to determining the oxygen saturation level of the patient is at or below the desaturation threshold, predict, using an oxygen saturation prediction model, whether the oxygen saturation level of the patient will increase above the desaturation threshold by the end of a predefined time period. In response to predicting that the oxygen saturation level of the patient will increase above the desaturation threshold by the end of the predefined time period, the processing circuitry refrains from outputting an indication of the patient experiencing an oxygen desaturation event.

33 Claims, 14 Drawing Sheets

(56) References Cited

U.S. PATENT DOCUMENTS

2015/0157275 A1   6/2015   Swamy et al.

OTHER PUBLICATIONS

International Search Report and Written Opinion of International Application No. PCT/US2021/052661, dated Jan. 28, 2022, 17 pp.
Lundberg et al., "Explainable Machine-Learning Predictions for the Prevention of Hypoxaemia During Surgery," Nature Biomedical Engineering, Nature Publishing Group UK, London, vol. 2., No. 10, Oct. 10, 2018, pp. 749-760, XP036610769, DOI: 10.1038/S41551-018-0304-0.

* cited by examiner

OXYGEN SATURATION MONITORING USING ARTIFICIAL INTELLIGENCE

BACKGROUND

Oxygen saturation monitoring systems are configured to monitor the oxygen saturation levels of a patient. In some examples, pulse oximetry sensors may be placed on a patient to measure the oxygen saturation level of the patient, such as by measuring photoplethysmograph (PPG) signals. When the oxygen saturation level of the patient decreases to reach a desaturation threshold, the oxygen saturation monitoring system may output an indication that the patient is experiencing oxygen desaturation.

SUMMARY

The present disclosure describes example devices, systems, and techniques for decreasing the amount of times that oxygen saturation monitoring systems may output an indication that a patient is experiencing oxygen desaturation based on a prediction of the future oxygen saturation levels of a patient. In examples described herein, when an oxygen saturation monitoring device determines that the oxygen saturation level of a patient has decreased to reach a desaturation threshold, the oxygen saturation monitoring device may predict whether the oxygen saturation level of the patient will increase back above the desaturation threshold within a predefined time period (e.g., on the order of seconds in some examples).

If the oxygen saturation monitoring device predicts that the oxygen saturation level of the patient will increase back above the desaturation threshold within the predefined time period, then the oxygen saturation monitoring device may refrain from outputting an indication that the patient is experiencing oxygen desaturation. At the end of the predefined time period, the oxygen saturation monitoring device may determine whether the oxygen saturation level of the patient has indeed increased back above the desaturation threshold. If the oxygen saturation monitoring device determines that the oxygen saturation level of the patient has not increased back above the desaturation threshold, then the oxygen saturation monitoring device may, at the end of the predefined time period, output an indication that the patient is experiencing oxygen desaturation.

By predicting whether the oxygen saturation level of the patient will increase back above the desaturation threshold within the predefined time period, the oxygen saturation monitoring device predicts whether the oxygen saturation level of the patient decreasing to reach the desaturation threshold is indicative of the patient experiencing a trivial desaturation event in which the oxygen saturation level of the patient may only briefly dip below the desaturation threshold before increasing back above the desaturation threshold. Because such trivial desaturation events may not be medically meaningful, e.g., may not be indicative of the occurrence of a medical event requiring intervention, outputting indications that the patient is experiencing oxygen desaturation in response to the patient experiencing such trivial desaturation events may not provide useful information to a clinician monitoring the health of the patient, and the indications may be a nuisance that unnecessarily distracts the clinician from performing other tasks.

By refraining from outputting an indication that the patient is experiencing oxygen desaturation if the oxygen saturation monitoring device predicts that the oxygen saturation level of the patient will increase back above the desaturation threshold within the predefined time period, the oxygen saturation monitoring device refrains from outputting an indication that the patient is experiencing a desaturation event if the oxygen saturation monitoring device predicts that the patient is merely experiencing a trivial desaturation event. In this way, the techniques described herein improve the functioning of the oxygen saturation monitoring device by reducing the number of times that the oxygen saturation monitoring device outputs an indication that the patient is experiencing oxygen desaturation in response to the patient experiencing trivial desaturation events.

In some examples, a method described herein includes receiving, by processing circuitry, a signal indicative of an oxygen saturation level of a patient. The method further includes determining, by the processing circuitry, that the signal indicates the oxygen saturation level is at or below a desaturation threshold. The method further includes in response to determining the oxygen saturation level of the patient is at or below the desaturation threshold, predicting, by the processing circuitry and using an oxygen saturation prediction model, whether the oxygen saturation level of the patient will increase above the desaturation threshold by the end of a predefined time period. The method further includes in response to predicting that the oxygen saturation level of the patient will increase above the desaturation threshold by the end of the predefined time period, refraining from outputting an indication of the patient experiencing an oxygen desaturation event.

In some examples, a system described herein includes an oxygen saturation sensing device configured to sense an oxygen saturation level of a patient. The system further includes processing circuitry configured to: receive a signal indicative of the oxygen saturation level of the patient; determining, by the processing circuitry, that the signal indicates the oxygen saturation level is at or below a desaturation threshold; in response to determining the oxygen saturation level of the patient is at or below the desaturation threshold, predict, using an oxygen saturation prediction model, whether the oxygen saturation level of the patient will increase above the desaturation threshold by the end of a predefined time period; and in response to predicting that the oxygen saturation level of the patient will increase above the desaturation threshold by the end of the predefined time period, refrain from outputting an indication of the patient experiencing an oxygen desaturation event.

In some examples, a non-transitory computer readable storable medium described herein comprises instructions that, when executed, cause processing circuitry to: receive a signal indicative of an oxygen saturation level of a patient; determining, by the processing circuitry, that the signal indicates the oxygen saturation level is at or below a desaturation threshold; in response to determining the oxygen saturation level of the patient is at or below the desaturation threshold, predict, using an oxygen saturation prediction model, whether the oxygen saturation level of the patient will increase above the desaturation threshold by the end of a predefined time period; and in response to predicting that the oxygen saturation level of the patient will increase above the desaturation threshold by the end of the predefined time period, refrain from outputting an indication of the patient experiencing an oxygen desaturation event.

The details of one or more examples are set forth in the accompanying drawings and the description below. Other features, objects, and advantages will be apparent from the description and drawings, and from the claims.

DETAILED DESCRIPTION

In general, aspects of the present disclosure describe devices, systems, and techniques for predicting the future oxygen saturation levels of a patient in ways that may decrease the amount of times that an oxygen saturation monitoring system may output an indication that a patient is experiencing oxygen desaturation. In examples described herein, when the oxygen saturation level of a patient has decreased to reach a desaturation threshold, an oxygen saturation monitoring device may predict whether the oxygen saturation level of the patient will increase back above the desaturation threshold within a predefined time period (e.g., on the order of seconds in some examples).

If the oxygen saturation monitoring device predicts that the oxygen saturation level of the patient will increase back above the desaturation threshold within the predefined time period, then the oxygen saturation monitoring device may refrain from outputting an indication that the patient is experiencing oxygen desaturation. At the end of the predefined time period, the oxygen saturation monitoring device may determine whether the oxygen saturation level of the patient has indeed increased back above the desaturation threshold. If the oxygen saturation monitoring device determines that the oxygen saturation level of the patient has not increased back above the desaturation threshold, then the oxygen saturation monitoring device may, at the end of the predefined time period, output an indication that the patient is experiencing oxygen desaturation.

Figure 1:
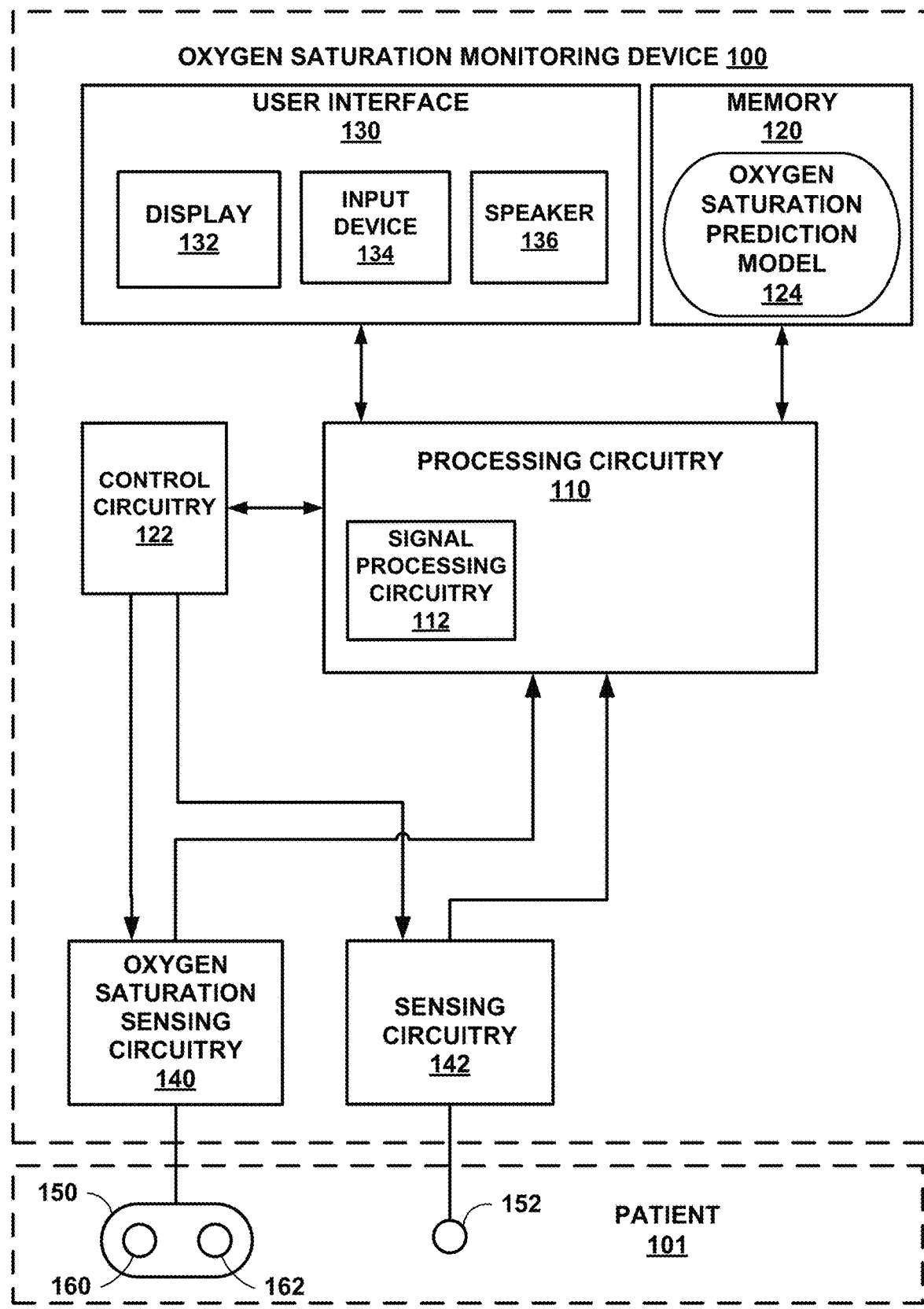
FIG. 1 is a conceptual block diagram illustrating an example oxygen saturation monitoring device.

FIG. 1 is a conceptual block diagram illustrating an example oxygen saturation monitoring device 100. Oxygen saturation monitoring device 100 includes processing circuitry 110, memory 120, control circuitry 122, user interface 130, sensing circuitry 140 and 142, and sensing devices 150 and 152. In the example shown in FIG. 1, user interface 130 may include display 132, input device 134, and/or speaker 136, which may be any suitable audio device including circuitry and configured to generate and output a noise.

In some examples, oxygen saturation monitoring device 100 may be configured to monitor and output (e.g., for display at display 132) the oxygen saturation level of patient 101, e.g., during a medical procedure or for more long-term monitoring, such as intensive care unit (ICU) and general post-operation monitoring. A clinician may receive information regarding the oxygen saturation level of a patient via user interface 130 and adjust treatment or therapy to patient 101 based on the information. Oxygen saturation monitoring device 100 may, for example, output the oxygen saturation level of patient 101 in graphical form, such as a graph of the oxygen saturation level of patient 101 over time, in textual form, such as outputting the oxygen saturation values of patient 101, in audible form, such as sounds indicative of the oxygen saturation level of patient 101, and the like.

Processing circuitry 110, as well as other processors, processing circuitry, controllers, control circuitry, and the like, described herein, may include one or more processors, and may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Control circuitry 122 may be operatively coupled processing circuitry 110. Control circuitry 122 is configured to control an operation of sensing devices 150 and 152. In some examples, control circuitry 122 may be configured to provide timing control signals to coordinate operation of sensing devices 150 and 152. For example, sensing circuitry 140 and 142 may receive from control circuitry 122 one or more timing control signals, which may be used by sensing circuitry 140 and 142 to turn on and off respective sensing devices 150 and 152, such as to collect data using sensing devices 150 and 152. In some examples, processing circuitry 110 may use the timing control signals to operate synchronously with sensing circuitry 140 and 142. For example, processing circuitry 110 may synchronize the operation of an analog-to-digital converter and a demultiplexer with sensing circuitry 140 and 142 based on the timing control signals.

Memory 120 may be configured to store, for example, monitored physiological parameter values, such as blood pressure values, oxygen saturation values, regional oxygen saturation values, or any combination thereof. Memory 120 may also be configured to store any other data that is collected by oxygen saturation monitoring device 100.

In some examples, memory 120 may store program instructions, such as neural network algorithms. The program instructions may include one or more program modules that are executable by processing circuitry 110. For example, memory 120 may store oxygen saturation prediction model 124, which may be a model trained via machine learning to predict whether the oxygen saturation level of patient 101 will increase above a desaturation threshold within a predefined time period. When executed by processing circuitry 110, such program instructions, such as program instructions of oxygen saturation prediction model 124, may cause processing circuitry 110 to provide the functionality ascribed to it herein. The program instructions may be embodied in software, firmware, and/or RAMware. Memory 120 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 may include a display 132, an input device 134, and a speaker 136. In some examples, user interface 130 may include fewer or additional components. User interface 130 is configured to present information to a user (e.g., a clinician). For example, user interface 130 and/or display 132 may include a monitor, cathode ray tube display, a flat panel display such as a liquid crystal (LCD) display, a plasma display, a light emitting diode (LED) display, and/or any other suitable display. In some examples, user interface 130 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

In some examples, processing circuitry 110 may be configured to present, by user interface 130, such as display 132, a graphical user interface to a user. The graphical user interface may include indications of values of one or more physiological parameters of a patient, such as, for example, blood pressure values, oxygen saturation values, regional oxygen saturation values, information about an autoregulation status (e.g., cerebral autoregulation status), pulse rate information, respiration rate information, other patient physiological parameters, or combinations thereof via display 132. User interface 130 may also include a device including circuitry configured to project audio to a user, such as speaker 136.

In some examples, processing circuitry 110 may also receive input signals from additional sources (not shown), such as a user. For example, processing circuitry 110 may receive from input device 134, such as a keyboard, a mouse, a touch screen, buttons, switches, a microphone, a joystick, a touch pad, or any other suitable input device or combination of input devices, an input signal. The input signal may contain information about patient 101, such as physiological parameters, treatments provided to patient 101, or the like. Additional input signals may be used by processing circuitry 110 in any of the determinations or operations it performs in accordance with processing circuitry 110.

In some examples, if processing circuitry 110 determines a particular status of patient 101 based on signals sensed by sensors 150, 152, or another sensing device, then processing circuitry 110 may present a notification indicating the detected status (e.g., a blood oxygen saturation at or below a desaturation threshold, as discussed below) via user interface 130. The notification may include a visual, audible, tactile, or somatosensory notification (e.g., an alarm signal) indicative of the abnormal status. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection.

Sensing circuitry 140 and 142 is configured to receive signals ("physiological signals") indicative of physiological parameters from respective sensing devices 150 and 152 and communicate the physiological signals to processing circuitry 110. Sensing devices 150 and 152 may include any sensing hardware configured to sense a physiological parameter of a patient, such as, but not limited to, one or more electrodes, optical receivers, blood pressure cuffs, or the like. The sensed physiological signals may include signals indicative of physiological parameters from a patient, such as, but not limited to, blood pressure, blood oxygen saturation (e.g., pulse oximetry and/or regional oxygen saturation), blood volume, heart rate, and respiration. For example, sensing circuitry 140 and 142 may include, but are not limited to, blood pressure sensing circuitry, blood oxygen saturation sensing circuitry, blood volume sensing circuitry, heart rate sensing circuitry, temperature sensing circuitry, electrocardiography (ECG) sensing circuitry, electroencephalogram (EEG) sensing circuitry, capnography sensing circuitry, spirometry sensing circuitry, or any combination thereof.

In some examples, sensing circuitry 140 and 142 and/or processing circuitry 110 may include signal processing circuitry 112 configured to perform any suitable analog conditioning of the sensed physiological signals. For example, sensing circuitry 140 and 142 may communicate to processing circuitry 110 an unaltered (e.g., raw) signal. Processing circuitry 110, e.g., signal processing circuitry 112, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of signal processing circuitry 112 to convert the conditioned analog signals into digital signals. In some examples, signal processing circuitry 112 may operate on the analog or digital form of the signals to separate out different components of the signals. In some examples, signal processing circuitry 112 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 112 may decrease the number of samples in the digital detector signals. In some examples, signal processing circuitry 112 may remove undesired or ambient contributions to the received signal. Additionally or alternatively, sensing circuitry 140 and 142 may include signal processing circuitry 112 to modify one or more raw signals and communicate to processing circuitry 110 one or more modified signals.

Oxygen saturation sensing device 150 (also referred to herein as blood oxygen saturation sensing device 150) is configured to generate an oxygen saturation signal indicative of blood oxygen saturation, such as $SpO_2$, within the venous, arterial, and/or capillary systems within a region of patient 101. For example, oxygen saturation sensing device 150 may include a sensor configured to non-invasively acquire a plethysmography (PPG) signal. One example of such a sensor may be one or more oximetry sensors (e.g., one or more pulse oximetry sensors) placed at one or multiple locations on patient 101, such as at a fingertip of patient 101, an earlobe of patient 101, and the like.

In some examples, oxygen saturation sensing device 150 may be configured to be placed on the skin of patient 101 to determine regional oxygen saturation of a particular tissue region, e.g., the frontal cortex or another cerebral location of patient 101. Oxygen saturation sensing device 150 may include emitter 160 and detector 162. Emitter 160 may include at least two light emitting diodes (LEDs), each configured to emit at different wavelengths of light, e.g., red or near infrared light. As used herein, the term "light" may refer to energy produced by radiative sources and may include any wavelength within one or more of the ultrasound, radio, microwave, millimeter wave, infrared, visible, ultraviolet, gamma ray or X-ray electromagnetic radiation spectra. In some examples, light drive circuitry (e.g., within sensing device 150, sensing circuitry 140, control circuitry 122, and/or processing circuitry 110) may provide a light drive signal to drive emitter 160 and to cause emitter 160 to emit light. In some examples, the LEDs of emitter 160 emit light in the range of about 600 nanometers (nm) to about 1000 nm. In a particular example, one LED of emitter 160 is configured to emit light at about 730 nm and the other LED of emitter 160 is configured to emit light at about 810 nm. Other wavelengths of light may be used in other examples.

Detector 162 may include a first detection element positioned relatively "close" (e.g., proximal) to emitter 160 and a second detection element positioned relatively "far" (e.g., distal) from emitter 160. In some examples, the first detection elements and the second detection elements may be chosen to be specifically sensitive to the chosen targeted energy spectrum of emitter 160. Light intensity of multiple wavelengths may be received at both the "close" and the "far" detector 162. For example, if two wavelengths are used, the two wavelengths may be contrasted at each location and the resulting signals may be contrasted to arrive at an oxygen saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). In operation, light may enter detector 162 after passing through the tissue of patient 101, including skin, bone, other shallow tissue (e.g., non-cerebral tissue and shallow cerebral tissue), and/or deep tissue (e.g., deep cerebral tissue). Detector 162 may convert the intensity of the received light into an electrical signal. The light intensity may be directly related to the absorbance and/or reflectance of light in the tissue. Surface data from the skin and skull may be subtracted out, to generate an oxygen saturation signal for the target tissues over time. Additional example details of an example device and technique for determining oxygen saturation based on light signals may be found in commonly assigned U.S. Pat. No. 9,861,317, which issued on Jan. 9, 2018, and is entitled "Methods and Systems for Determining Regional Blood Oxygen Saturation."

Oxygen saturation sensing device 150 may provide the oxygen saturation signal to processing circuitry 110 or to any other suitable processing device for use in monitoring the oxygen saturation level of patient 101. One example of such an oxygen saturation signal may be a plethysmography (PPG) signal. Another example is a regional oxygen saturation ($rSO_2$) signal indicative of blood oxygen saturation within the venous, arterial, and/or capillary systems within a region of the patient.

In operation, blood pressure sensing device 152 and oxygen saturation sensing device 150 may each be placed on the same or different parts of the body of patient 101. For example, blood pressure sensing device 152 and oxygen saturation sensing device 150 may be physically separate from each other and may be separately placed on patient 101. As another example, blood pressure sensing device 152 and oxygen saturation sensing device 150 may in some cases be supported by a single sensor housing. One or both of blood pressure sensing device 152 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example oxygen saturation monitoring device 100 is shown in FIG. 1, the components illustrated in FIG. 1 are not intended to be limiting. Additional or alternative components and/or implementations may be used in other examples.

Blood pressure sensing device 152 is configured to generate a blood pressure signal indicative of a blood pressure of patient 101. For example, blood pressure sensing device 152 may include a blood pressure cuff configured to non-invasively sense blood pressure or an arterial line configured to invasively monitoring blood pressure in an artery of patient 101. In some examples, the blood pressure signal may include at least a portion of a waveform of the acquisition blood pressure. Blood pressure sensing device 152 may be configured to generate a blood pressure signal indicative of the blood pressure of patient over time. Blood pressure sensing device 152 may provide the blood pressure signal to sensing circuitry 142, processing circuitry 110, or to any other suitable processing device, which may be part of device 100 or a device separate from device 100, such as another device co-located with device 100 or remotely located relative to device 100.

Processing circuitry 110 may be configured to receive one or more signals generated by sensing devices 150 and 152 and sensing circuitry 140 and 142. The physiological signals may include a signal indicating blood pressure and/or a signal, such as a PPG signal or a brain regional oxygen saturation (rSO2) signal, indicating oxygen saturation. Processing circuitry 110 may be configured to predict the oxygen saturation levels of patient 101 in the future based on these signals.

Processing circuitry 110 of oxygen saturation monitoring device 100 may be configured to monitor the oxygen saturation level of patient 101. Processing circuitry 110 of oxygen saturation monitoring device 100 may continuously obtain the oxygen saturation level of patient 101 over time using, for example, the PPG signals generated by sensing devices 150 and 152 and/or sensing circuitry 140 and 142, and may provide an indication of the oxygen saturation level of patient 101 via user interface 130. For example, processing circuitry 110 of oxygen saturation monitoring device 100 may output, at display 132, a graphical representation of the oxygen saturation level of patient 101.

In some examples, the oxygen saturation level of patient 101 may be expressed as a percentage (e.g., from 0% to 100%) of oxygen-saturated hemoglobin relative to total hemoglobin in the blood of patient 101, and processing circuitry 110 of oxygen saturation monitoring device 100 may be configured to monitor the oxygen saturation level of patient 101 for oxygen desaturation events experienced by patient 101. For example, processing circuitry 110 is configured to monitor the oxygen saturation level based on signals received from oxygen saturation sensing circuitry 140. Patient 101 may experience an oxygen desaturation event when the oxygen saturation level of patient 101 decreases to or below a desaturation threshold. Examples of desaturation thresholds may be 90%, 85%, and the like. Thus, processing circuitry 110 may determine that patient 101 is experiencing an oxygen desaturation event in response to determining the oxygen saturation level of patient 101 decreases to 90%, e.g., is at or below 90%, or other desaturation threshold. The desaturation threshold indicative of an oxygen desaturation event may be stored by memory 120 and can be specific to patient 101 or may be used for a population of patients.

Because the occurrence of oxygen desaturation may indicate the occurrence of a medical event that requires clinician intervention, processing circuitry 110 of oxygen saturation monitoring device 100 may output a notification (e.g., an alarm) indicative of an oxygen desaturation event each time processing circuitry 110 determines that the oxygen saturation level of patient 101 decreases from being above the desaturation threshold to reach the desaturation threshold (e.g., is at or below the desaturation threshold) in order to alert a clinician to the occurrence of the oxygen desaturation event. Such a notification may be in the form of textual or graphical information outputted by display 132, audio outputted by speaker 136, or the like.

However, not every oxygen desaturation event may be indicative of patient 101 experiencing a medical event that may require clinician intervention. For example, the oxygen saturation level of patient 101 may increase back up above the desaturation threshold relatively shortly (e.g., within a few seconds) after decreasing to at or below the desaturation threshold, and such relatively short periods of oxygen desaturation may not be indicative of an occurrence of a medical event that may require clinician intervention. While it may be unnecessary to output a notification indicative of patient 101 experiencing such a trivial oxygen desaturation event, it may be challenging to determine, at the time an oxygen desaturation event occurs, whether the oxygen desaturation event is a trivial oxygen desaturation event or a desaturation event that may be more likely to require medical intervention (also referred to herein as a "non-trivial desaturation event").

In accordance with aspects of the present disclosure, processing circuitry 110 of oxygen saturation monitoring device 100 is configured to monitor the oxygen saturation levels of patient 101 in ways that potentially reduce the number of times that oxygen saturation monitoring device 100 outputs notifications indicative of oxygen desaturation events experienced by patient 101 by predicting whether a detected oxygen desaturation event is a trivial oxygen desaturation event or a non-trivial desaturation event. Instead of outputting a notification indicative of an oxygen desaturation event each time the oxygen saturation level of patient 101 decreases from being above a desaturation threshold to at or below the desaturation threshold, processing circuitry 110 of oxygen saturation monitoring device 100 is configured to, in response to the oxygen saturation level of the patient 101 decreasing to reach the desaturation threshold, predict, using oxygen saturation prediction model 124, whether the oxygen saturation level of patient 101 will increase above the desaturation threshold by the end of a predefined time period immediately following the prediction. Such a predefined time period may be relatively short, such as 5 seconds, 10 seconds, 15 seconds, 20 seconds, or the like. Note that in some examples, processing circuitry 110 may not necessarily perform the prediction at the exact moment that the oxygen saturation level of the patient 101 decreases to reach the desaturation threshold. Instead, processing circuitry 110 may perform the prediction substantially at the time that the oxygen saturation level of the patient 101 reaches the desaturation threshold, such as within a second, within 3 seconds, and the like, after the oxygen saturation level of the patient 101 reaches the desaturation threshold.

If processing circuitry 110 predicts that the oxygen saturation level of patient 101 will increase above the desaturation threshold by the end of the predefined time period, then processing circuitry 110 in effect determines that a detected desaturation event is a trivial oxygen desaturation event, and may therefore be configured to refrain from outputting a notification indicative of patient 101 experiencing an oxygen desaturation event. Instead, processing circuitry 110 may be configured to determine, at the end of the predefined time period, whether to output a notification indicative of an oxygen desaturation event. That is, if processing circuitry 110 predicts that the oxygen saturation level of patient 101 will increase above the desaturation threshold by the end of the predefined time period, processing circuitry 110 of oxygen saturation monitoring device 100 may be configured to, at the end of the predefined time period and using oxygen saturation prediction model, determine whether the oxygen saturation level of patient 101 has actually increased above the desaturation threshold is correct.

For example, if processing circuitry 110 predicts that the oxygen saturation level of patient 101 will increase above the desaturation threshold by the end of the predefined time period, then processing circuitry 110 determines, at the end of the predefined time period, whether the oxygen saturation level of patient 101 is indeed above the desaturation threshold based on a signal from oxygen saturation sensing circuitry 140 and indicative of an oxygen saturation level of patient 101 sensed by sensor 150. If processing circuitry 110 determines that the oxygen saturation level of patient 101 is above the desaturation threshold at the end of the predetermined time period, then processing circuitry 110 refrains from outputting a notification indicative of patient 101 experiencing an oxygen desaturation event. Conversely, if processing circuitry 110 determines that the oxygen saturation level of patient 101 is not above the desaturation threshold at the end of the predetermined time period, then processing circuitry 110 may be configured to output a notification indicative of patient 101 experiencing an oxygen desaturation event.

Thus, even when processing circuitry 110 incorrectly predicts that oxygen saturation level of patient 101 will increase above the desaturation threshold by the end of a predefined time period, oxygen saturation monitoring device 100 may still, at the end of the predefined period, output a notification (e.g., an alarm) indicative of patient 101 experiencing an oxygen desaturation event upon determining that the oxygen saturation level of patient 101 has not increased above the desaturation threshold. Because the predefined time period may be relatively short (e.g., 10 seconds), such a short delay in outputting a notification indicative of patient 101 experiencing an oxygen desaturation event may not adversely affect a clinician's ability to address such desaturation events in a timely manner. In this way, processing circuitry 110 may be configured to reduce nuisance alerts indicative of trivial oxygen desaturation events while still providing timely indications of more non-trivial desaturation events.

In some examples, processing circuitry 110 is configured to predict whether the oxygen saturation level of patient 101 will increase above the desaturation threshold by the end of a predefined time period based at least in part on information associated with patient 101 over time during a time period, such as 60 seconds, immediately prior to the blood oxygen saturation level of patient 101 decreasing to reach the desaturation threshold. For example, processing circuitry 110 may be configured to predict whether the oxygen saturation level of patient 101 will increase above the desaturation threshold by the end of a predefined time period based at least in part on information associated with patient 101 over time during a time period prior to the blood oxygen saturation level of patient 101 decreasing to reach the desaturation threshold based at least on part on one or more of: the oxygen saturation levels of patient 101 provided by, for example, oxygen saturation sensing device 150, over a time period, the blood pressure of patient 101 provided by, for example, blood pressure sensing device 152, over a time period, and/or one or more metrics derived from the PPG signals of patient 101 provided by, for example, oxygen saturation sensing device 150, over a time period prior to the blood oxygen saturation level of patient 101 decreasing to reach the desaturation threshold.

The point in time at which processing circuitry 110 predicts whether the oxygen saturation level of patient 101 will increase above the desaturation threshold by the end of a predefined time period may be referred to herein as the prediction point, and processing circuitry 110 may be configured to determine and/or receive, over a time period immediately preceding the prediction point, information such as one or more of: the history of the oxygen saturation levels of patient 101 during the time period immediately preceding the prediction point, the history of blood pressure values of patient 101 during the time period, and/or one or more metrics derived from the PPG signals of patient 101 during the time period. Examples of such a time period immediately preceding the prediction point may be 60 seconds, 20 seconds, 100 seconds, and the like.

Processing circuitry 110 may be configured to continuously determine the blood pressure of patient 101 during the time period by periodically receiving the blood pressure of patient 101 from blood pressure sensing device 152, such as every second, every five seconds, every minute, and the like. For example, oxygen saturation monitoring device 100 may periodically turn on or activate blood pressure sensing device 152 so that blood pressure sensing device 152 may measure the blood pressure of patient 101. In another example, processing circuitry 110 may be configured to continually monitor the blood pressure of patient 101, and oxygen saturation monitoring device 100 may periodically request the blood pressure of patient 101 from blood pressure sensing device 152.

Similarly, in some examples, processing circuitry 110 of oxygen saturation monitoring device 100 may be configured to continuously determine the oxygen saturation level of patient 101 during the time period by continuously receiving on the oxygen saturation level of patient 101 from oxygen saturation sensing device 150, such as in the form of a PPG signal. Processing circuitry 110 may also be configured to extract features, such as a set of metrics, from the PPG signal received by processing circuitry 110 during the time period. For example, the features may include the values of any combination of one or more of PPG pulse skews, PPG pulse amplitudes, normalized amplitudes of PPG pulses, PPG pulse maximum slope, the location of the PPG pulse maximum slope, PPG pulse maximum curvature, the location of the PPG pulse maximum curvature, or any other suitable morphological parameters derived from the PPG signal.

Processing circuitry 110 is configured to predict, at the prediction time or another time prior to the end of a predefined period, whether the oxygen saturation level of patient 101 will increase above the desaturation threshold by the end of the predefined time period by using oxygen saturation prediction model 124, such as by predicting the oxygen saturation level of patient 101 at the end of the predefined time period. In some examples, oxygen saturation prediction model 124 include one or more neural network algorithms trained via machine learning to take one or more of: the oxygen saturation levels of patient 101, the blood pressure of patient 101, and/or one or more metrics derived from the PPG signals of patient 101 determined during a time period immediately preceding the prediction point as inputs to predict the oxygen saturation level of patient 101 at the end of the predefined time period.

A neural network algorithm, or artificial neural network, may include a trainable or adaptive algorithm utilizing nodes that define rules. For example, a respective node of a plurality of nodes may utilize a function, such as a non-linear function or if-then rules, to generate an output based on an input. A respective node of the plurality of nodes may be connected to one or more different nodes of the plurality of nodes along an edge, such that the output of the respective node includes the input of the different node. The functions may include parameters that may be determined or adjusted using a training set of inputs and desired outputs, such as, for example, a predetermined association between one or more signals, such as one or more of: the oxygen saturation levels of patient 101, the blood pressure of patient 101, and/or one or more metrics derived from the PPG signals of patient 101, along with a learning rule, such as a back-propagation learning rule. The back-propagation learning rule may utilize one or more error measurement comparing the desired output to the output produced by the neural network algorithm to train the neural network algorithm by varying the parameters to minimize the one or more error measurements.

An example neural network includes a plurality of nodes, at least some of the nodes having node parameters. An input including one or more of: the oxygen saturation levels of patient 101, the blood pressure of patient 101, and/or one or more metrics derived from the PPG signals of patient 101 may be input to a first node of the neural network algorithm. In some examples, the input may include a plurality of inputs, each input into a respective node. The first node may include a function configured to determine an output based on the input and one or more adjustable node parameters. In some examples, the neural network may include a propagation function configured to determine an input to a subsequent node based on the output of a preceding node and a bias value. In some examples, a learning rule may be configured to modify one or more node parameters to produce a favored output. For example, the favored output may be constrained by one or more threshold values and/or to minimize one or more error measurements. The favored output may include an output of a single node, a set of nodes, or the plurality of nodes.

The neural network algorithm may iteratively modify the node parameters until the output includes the favored output. In this way, processing circuitry 110 may be configured to iteratively evaluating outputs of the neural network algorithm and iteratively modifying at least one of the node parameters based on the evaluation of the outputs of the neural network algorithm to predict the oxygen saturation level of a patient, such as patient 101, at or within a predefined future time period based on the modified neural network algorithm. In some examples, a neural network algorithm may enable processing circuitry 110 to more accurately predict the oxygen saturation level of patient 101 based on one or more of: the oxygen saturation levels of patient 101, the blood pressure of patient 101, and/or one or more metrics derived from the PPG signals of patient 101 compared to other techniques and/or reduce computational time and/or power required to predict future oxygen saturation levels of patient 101.

In accordance with aspects of the present disclosure, when processing circuitry 110 determines that the oxygen saturation level of patient 101 decreases to reach a desaturation threshold, processing circuitry 110 may be configured to execute oxygen saturation prediction model 124 to predict whether the oxygen saturation level of patient 101 will increase above the desaturation threshold by the end of a predefined time period. Processing circuitry 110 may be configured to input, into oxygen saturation prediction model 124, one or more of: a history of the oxygen saturation levels of patient 101 over a time period immediately preceding the prediction point, a history of the blood pressure values of patient 101 over the time period, and/or one or more metrics derived from the PPG signals of patient 101 over the time period.

Processing circuitry 110 may be configured to execute oxygen saturation prediction model 124 to predict whether the oxygen saturation level of patient 101 will increase above the desaturation threshold by the end of a predefined time period. If processing circuitry 110 predicts that the oxygen saturation level of patient 101 will not increase above the desaturation threshold by the end of the predefined time period, then processing circuitry may be configured to output, at user interface 130, a notification indicative of an oxygen desaturation event for patient 101. For example, processing circuitry 110 may be configured to output a visual indication of an oxygen desaturation event for patient 101 at display 132, or may output an audible indication of an oxygen desaturation event for patient 101 via speaker 136.

If processing circuitry 110 predicts that the oxygen saturation level of patient 101 will increase above the desaturation threshold by the end of the predefined time period, then processing circuitry may be configured to refrain from outputting a notification indicative of an oxygen desaturation event for patient 101. Instead, at the end of the predefined time period (e.g., immediately after the predefined period), processing circuitry 110 may determine whether the oxygen saturation level of patient 101 has increased above the desaturation threshold, e.g., based on signals received from oxygen saturation sensing circuitry 140 and indicative of actual sensed oxygen saturation levels sensed by oxygen saturation sensor 150. If processing circuitry 110 determines that the oxygen saturation level of patient 101 has not increased above the desaturation threshold by the end of the predefined time period, then processing circuitry 110 may output, at user interface 130, a notification indicative of an oxygen desaturation event for patient 101. For example, processing circuitry 110 may be configured to output a visual indication of an oxygen desaturation event for patient 101 at display 132, or may output an audible indication of an oxygen desaturation event for patient 101 via speaker 136.

On the other hand, if processing circuitry 110 determines that the oxygen saturation level of patient 101 has increased above the desaturation threshold by the end of the predefined time period, then processing circuitry 110 refrains from (i.e., does not) output, at user interface 130, a notification indicative of an oxygen desaturation event for patient 101. In this way, oxygen saturation monitoring device 100 is still configured to provide monitoring of patient 101 and indications indicative of a patient event such as an oxygen desaturation event, while reducing nuisance notifications that may gain the attention of a clinician but are not indicative of a patient event that requires clinician intervention.

In some examples, oxygen saturation monitoring device 100, e.g., processing circuitry 110 or user interface 130, may include a communication interface to enable oxygen saturation monitoring device 100 to exchange information with external devices. The communication interface may include any suitable hardware, software, or both, which may allow oxygen saturation monitoring device 100 to communicate with electronic circuitry, a device, a network, a server or other workstations, a display, or any combination thereof. For example, processing circuitry 110 may receive blood pressure values, oxygen saturation values, capnography values, spirometry values, and the like from an external device via the communication interface.

In some examples, instead of determining a single prediction of whether the oxygen saturation level of patient 101 will increase above the desaturation threshold by the end of a predefined time period, processing circuitry 110 is configured to determine a plurality of predictions of whether the oxygen saturation level of patient 101 will increase above the desaturation threshold by the end of a predefined time period. Processing circuitry 110 may determine, based on the plurality of predictions, whether the oxygen saturation level of patient 101 will increase above the desaturation threshold by the end of a predefined time period, e.g., to detect an oxygen saturation event.

Using such an ensemble of predictions generated by one or more different neural networks having different neural network configurations and initialized in different ways may result in a diversity of predictions compared with a prediction generated using a single oxygen saturation prediction model. Such a diversity of predictions may potentially improve the accuracy of oxygen saturation monitoring device 100 in predicting whether the oxygen saturation level of patient 101 will increase above the desaturation threshold by the end of a predefined time period.

For example, if oxygen saturation monitoring device 100 determines whether the oxygen saturation level of patient 101 will increase above the desaturation threshold by the end of a predefined time period based on a single prediction, oxygen saturation monitoring device 100 may be unable to determine whether the single prediction is an outlier prediction that is likely to be an inaccurate prediction of whether the oxygen saturation level of patient 101 will increase above the desaturation threshold by the end of a predefined time period based on a single prediction. In contrast, when oxygen saturation monitoring device 100 uses an ensemble of predictions to determine whether the oxygen saturation level of patient 101 will increase above the desaturation threshold by the end of a predefined time period, oxygen saturation monitoring device 100 may be able to determine whether a prediction is an outlier prediction by comparing the prediction against the other predictions in the ensemble of predictions, thereby enabling oxygen saturation monitoring device 100 to refrain from using such outlier predictions to determine whether the oxygen saturation level of patient 101 will increase above the desaturation threshold by the end of a predefined time period.

In some examples, oxygen saturation prediction model 124 comprises a plurality of oxygen saturation prediction models in the form of a plurality of neural network algorithms, such as the neural network algorithm described above, which are trained via machine learning to each take one or more of: the oxygen saturation levels of patient 101, the blood pressure of patient 101, and/or one or more metrics derived from the PPG signals of patient 101 determined during a time period immediately preceding the prediction point as inputs to predict the oxygen saturation level of patient 101 at the end of the predefined time period. In some examples, each of the plurality of oxygen saturation prediction models may be trained using a different set of inputs to predict the oxygen saturation level of patient 101 at the end of the predefined time period.

In some examples, the plurality of oxygen saturation prediction models may include neural network algorithms having different network configurations, such as a combination of one or more of: a long short-term memory (LSTM) model, a convolutional neural network (CNN), and the like having the same or different hyperparameters. In other examples, processing circuitry 110 may utilize a single model of oxygen saturation prediction model 124 to generate plurality of predictions of whether the oxygen saturation level of patient 101 will increase above the desaturation threshold by the end of a predefined time period. For example, processing circuitry 110 may run different oxygen saturation prediction models 124 that have been trained using different random number seeds and/or starting conditions to generate the plurality of predictions. In some examples, the plurality of oxygen saturation prediction models may have different configurations of hyperparameters, such as by including different number of units in the bidirectional long short-term memory (BiLSTM) layers of the oxygen saturation prediction models.

Processing circuitry 110 may be configured to determine an average predicted oxygen saturation level by the end of the predefined time period from two or more of the plurality of predictions and may be configured to predict, based at least in part on the average predicted oxygen saturation level by the end of the predefined time period, whether the oxygen saturation level of patient 101 will increase above the desaturation threshold by the end of a predefined time period. For example, given N predicted oxygen saturation levels generated by one or more oxygen saturation predictions models of oxygen saturation prediction model 124, processing circuitry 110 may be configured to average two or more of the N predicted oxygen saturation levels to determine an average predicted oxygen saturation level.

In some examples, processing circuitry 110 may be configured to select two or more predicted oxygen saturation levels to be averaged out of the plurality of predicted oxygen saturation levels based on the two or more predicted oxygen saturation levels being within a specified percentile of the plurality of predicted oxygen saturation levels. A percentile may be the value below which a given percentage of observations in a group of observations falls, where the highest predicted oxygen saturation level out of the plurality of predicted oxygen saturation levels would be at the highest percentile (e.g., $99^{th}$ percentile), and the lowest predicted oxygen saturation level out of the plurality of predicted oxygen saturation levels would be at the lowest percentile (e.g., $1^{st}$ percentile). For example, processing circuitry 110 may be configured to select predicted oxygen saturation levels that are within a range of percentiles, such as between $25^{th}$ and $50^{th}$ percentile or predicted oxygen saturation levels that are at a specified percentile, such as predicted oxygen saturation levels at the $50^{th}$ percentile. In some examples, if processing circuitry 110 is biased towards higher predicted oxygen saturation levels, then processing circuitry 110 may be configured to select predicted oxygen saturation levels that are within a range of percentiles, such as the bottom $50^{th}$ percentile. In other examples, if processing circuitry 110 is biased towards lower predicted oxygen saturation levels, processing circuitry 110, processing circuitry 110 may be configured to select predicted oxygen saturation levels that are within a range of percentiles, such as between $50^{th}$ and $75^{th}$ percentile.

In some examples, processing circuitry 110 may be configured to determine whether the plurality of select predicted oxygen saturation levels includes an outlier prediction and, if so, refrain from including the outlier in the two or more of the plurality of predicted oxygen saturation levels to be averaged to determine an average predicted oxygen saturation level. Processing circuitry 110 may be able to determine that a predicted oxygen saturation level is an outlier prediction based on determining the difference between the predicted oxygen saturation level and the other predicted oxygen saturation levels in the plurality of predicted oxygen saturation levels. For example, processing circuitry 110 may be configured to determine that a predicted oxygen saturation level is an outlier if the distance from the predicted oxygen saturation level to the median of the plurality of predicted oxygen saturation level is much greater (e.g., more than 2× greater, more than 3× greater, etc.) than the median distance of the plurality of predicted oxygen saturation level to the median of the plurality of predicted oxygen saturation levels.

Processing circuitry 110 may therefore be configured to determine whether the average predicted oxygen saturation level is above the desaturation threshold. If processing circuitry 110 determines that the average predicted oxygen saturation level is above the desaturation threshold, then processing circuitry 110 may determine that the oxygen saturation level of patient 101 will increase above the desaturation threshold by the end of a predefined time period. If processing circuitry 110 determines that the average predicted oxygen saturation level is not above the desaturation threshold, then processing circuitry 110 may determine that the oxygen saturation level of patient 101 will not increase above the desaturation threshold by the end of a predefined time period.

In some examples, processing circuitry 110 may be configured to determine the average predicted oxygen saturation level by the end of the predefined time period from two or more of the plurality of predictions by performing a weighted average of two or more of the N predicted oxygen saturation levels to skew the predicted oxygen saturation level and determine a weighted average predicted oxygen saturation level. For example, processing circuitry 110 may determine a weight, which may be a number between 0 and 1, for each predicted oxygen saturation level of the two or more of the predicted oxygen saturation levels to be averaged. Processing circuitry 110 may multiply each predicted oxygen saturation level with the corresponding weight to determine a plurality of weighted predicted oxygen saturation levels, and may determine the average of the plurality of weighted predicted oxygen saturation levels to determine a weighted average predicted oxygen saturation level.

Processing circuitry 110 can be configured to apply different weights to different predicted oxygen saturation levels. In some examples, if processing circuitry 110 is biased towards lower predicted oxygen saturation levels, then processing circuitry 110 may be configured to assign smaller weights to the lower predicted oxygen saturation levels and to assign larger weights to the higher predicted oxygen saturation levels. In some examples, if processing circuitry 110 is biased towards higher predicted oxygen saturation levels, then processing circuitry 110 may be configured to assign larger weights to the lower predicted oxygen saturation levels and to assign smaller weights to the higher predicted oxygen saturation levels.

In some examples, processing circuitry 110 may determine weights for each of the two or more predicted oxygen saturation levels based on the accuracy of the oxygen saturation prediction models that generates the predicted oxygen saturation levels. If processing circuitry 110, for example, determines that an oxygen saturation prediction model is consistently better than other oxygen saturation prediction models, then processing circuitry 110 may be configured to assign a larger weight to a predicted oxygen saturation level generated by the oxygen saturation prediction model compared with the predicted oxygen saturation levels generated by the other oxygen saturation prediction models.

In some examples, the larger weights assigned to predicted oxygen saturation levels determined by a consistently accurate oxygen saturation prediction model may be conditional on the value of the predicted oxygen saturation level determined by the oxygen saturation prediction model. For example, if processing circuitry 110 determines that an oxygen saturation prediction model is better at predicting deep desaturation events (i.e., determining that the predicted oxygen saturation level is at or below a deep desaturation threshold, which can be different from a desaturation threshold and indicative of a more physiologically significant even than an oxygen desaturation event), then processing circuitry 110 may assign a larger weight to a predicted oxygen saturation level determined by the oxygen saturation prediction model only if the predicted oxygen saturation level is at or below the deep desaturation threshold.

In some examples, processing circuitry 110 may be configured to perform a robust curve fit, such as a robust polynomial regression, a robust linear regression, and the like to the two or more predicted oxygen saturation levels. The robust method may include, for example, the square of the distance to the median, the median square of the distance to the median, and the like. Processing circuitry 110 may be configured to determine an amount of skew to apply to the two or more predicted oxygen saturation levels as the difference between the calculated robust curve fit and the line of unity. For example, the amount of skew may be a weight that processing circuitry 110 may be configured to multiply against the predicted oxygen saturation levels.

In some examples, processing circuitry 110 may be configured to perform a robust curve fit for each of the two or more predicted oxygen saturation levels. Processing circuitry 110 may be configured to determine an amount of skew to apply to each of the two or more predicted oxygen saturation levels, apply the determined amount of skew to each of the two or more predicted oxygen saturation levels, and determine an average of the skewed two or more predicted oxygen saturation levels.

In some examples, processing circuitry 110 may be configured to perform a robust curve fit for the average predicted oxygen saturation level of the two or more predicted oxygen saturation levels. Processing circuitry 110 may be configured to determine an amount of skew to apply to the average predicted oxygen saturation level and apply the determined amount of skew to the average predicted oxygen saturation level.

In some examples, processing circuitry 110 may be configured to add or subtract a bias to the average predicted oxygen saturation level to determine a biased average predicted oxygen saturation level. The bias may be a delta in oxygen saturation level, such as represented by $\Delta SpO_2$, that processing circuitry 110 may add to or subtract from the average predicted oxygen saturation level to determine a biased average predicted saturation level. The bias can be predetermined and stored by memory 120 of oxygen saturation monitoring device 100 or a memory of another device.

Processing circuitry 110 may therefore be configured to determine, based on the biased average predicted oxygen saturation level, whether the oxygen saturation level of patient 101 will increase above the desaturation threshold by the end of a predefined time period. For example, processing circuitry 110 may be configured to determine whether the biased average predicted oxygen saturation level is above the desaturation threshold. If processing circuitry 110 determines that the biased average predicted oxygen saturation level is above the desaturation threshold, then processing circuitry 110 may determine that the oxygen saturation level of patient 101 will increase above the desaturation threshold by the end of a predefined time period. If processing circuitry 110 determines that the biased average predicted oxygen saturation level is not above the desaturation threshold, then processing circuitry 110 may determine that the oxygen saturation level of patient 101 will not increase above the desaturation threshold by the end of a predefined time period.

In some examples, processing circuitry 110 may be configured to add or subtract a bias to a weighted average predicted oxygen saturation level to determine a biased and weighted average predicted oxygen saturation level. Processing circuitry 110 may therefore be configured to determine, based on the biased and weighted average predicted oxygen saturation level, whether the oxygen saturation level of patient 101 will increase above the desaturation threshold by the end of a predefined time period. For example, processing circuitry 110 may be configured to determine whether the biased and weighted average predicted oxygen saturation level is above the desaturation threshold. If processing circuitry 110 determines that the biased and weighted average predicted oxygen saturation level is above the desaturation threshold, then processing circuitry 110 may determine that the oxygen saturation level of patient 101 will increase above the desaturation threshold by the end of a predefined time period. If processing circuitry 110 determines that the biased and weighted average predicted oxygen saturation level is not above the desaturation threshold, then processing circuitry 110 may determine that the oxygen saturation level of patient 101 will not increase above the desaturation threshold by the end of a predefined time period.

In some examples, a training system may alter the degree of skew (e.g., weights) and bias during model training of oxygen saturation prediction model 124 to help improve the predicting the desaturation threshold of patient 101 by the end of a predefined time period. For example, oxygen saturation prediction model 124 may be trained to minimize the number of incorrect predicted oxygen saturation levels where the predicted oxygen saturation level is above the desaturation threshold and the actual oxygen saturation level of patient 101 at the end of the predefined time period is at or below a deep desaturation threshold. In another example, oxygen saturation prediction model 124 may be trained to maximize the number of times the predicted oxygen saturation level and the actual oxygen saturation level of patient 101 are both above the desaturation threshold. In this way, the predictive techniques disclosed herein can be tuned through incremental adjustments to skew and bias.

The components of oxygen saturation monitoring device 100 that are shown and described as separate components are shown and described as such for illustrative purposes only. In some examples the functionality of some of the components may be combined in a single component. For example, the functionality of processing circuitry 110 and control circuitry 122 may be combined in a single processor system. Additionally, in some examples the functionality of some of the components of oxygen saturation monitoring device 100 shown and described herein may be divided over multiple components. For example, some or all of the functionality of control circuitry 122 may be performed in processing circuitry 110, or sensing circuitry 140 and 142. In other examples, the functionality of one or more of the components may be performed in a different order or may not be required.

Figure 2:
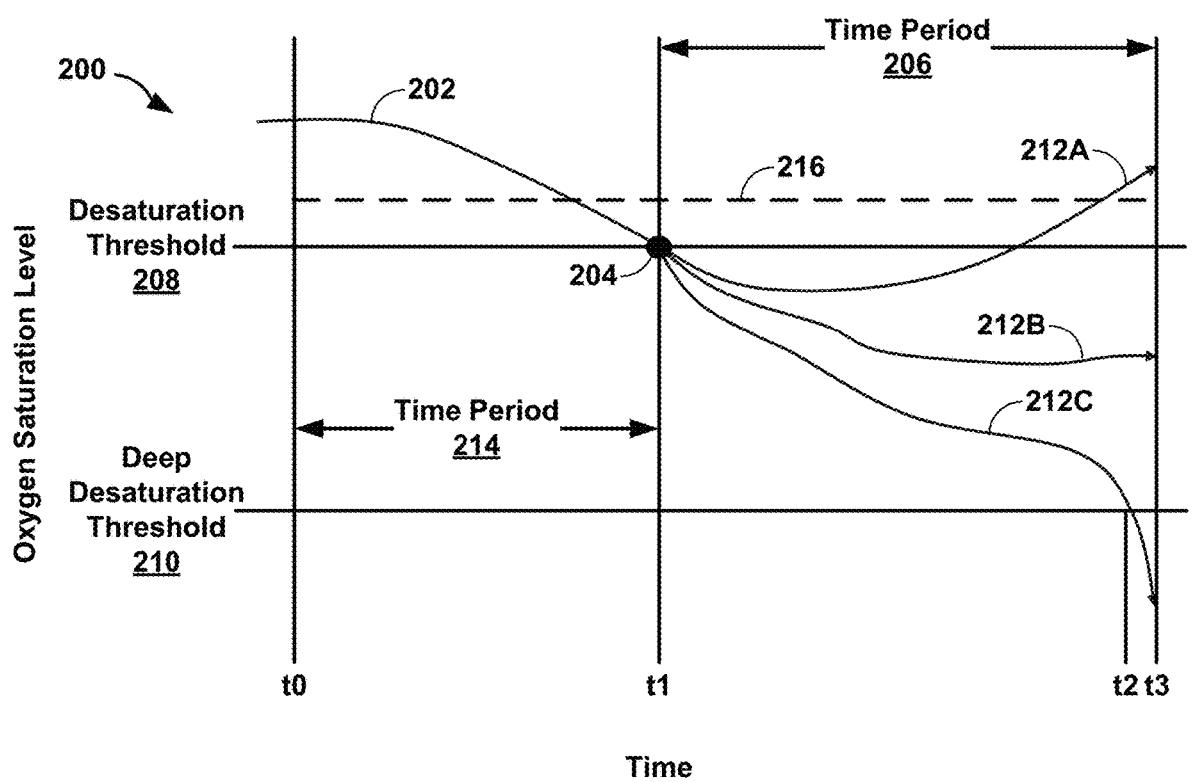
FIG. 2 illustrates an example graph of the oxygen saturation level of a patient before and after the oxygen saturation level of the patient decreases to reach a desaturation threshold.

FIG. 2 illustrates an example graph 200 of the oxygen saturation level of a patient before and after the oxygen saturation level of the patient decreases to reach a desaturation threshold. As shown in FIG. 2, in graph 200, oxygen saturation level 202 of patient 101 may decrease over time from being above desaturation threshold 208 to reach desaturation threshold 208 at time t1. When oxygen saturation level 202 of patient 101 reaches desaturation threshold 208, oxygen saturation level 202 of patient 101 may either continue to decrease, such as according to oxygen saturation curves 212B and 212C, so that oxygen saturation level 202 of patient 101 is below desaturation threshold 208 at the end of time period 206, or may eventually increase, such as according to oxygen saturation curve 212A, so that oxygen saturation level 202 of patient 101 is above desaturation threshold 208 at the end of time period 206. Time period 206 may be a predefined time period set by a clinician or a manufacturer of device 100 and may be stored in memory 120 (FIG. 1). In some examples, processing circuitry 110 is configured to select time period 206 from a plurality of stored time periods based on one or more factors, such as, but not limited to, user input received via user interface 130 selecting a time period, patient 101 parameters (e.g., age, body mass index (BMI), or the like).

Because it is possible that oxygen saturation level 202 of patient 101 that decreases to reach desaturation threshold 208 may return shortly (e.g., by the end of time period 206) to being above desaturation threshold 208, oxygen saturation monitoring device 100 may, when oxygen saturation level 202 of patient 101 decreases to reach desaturation threshold 208, refrain from immediately outputting a notification indicative of a desaturation event, e.g., indicating that oxygen saturation level 202 of patient 101 has reached desaturation threshold 208. Instead, as discussed above, processing circuitry 110 of oxygen saturation monitoring device 100 may use oxygen saturation prediction model 124 to predict whether oxygen saturation level 202 of patient 101 will increase above desaturation threshold 208 at the end of time period 206, such as shown by oxygen saturation curve 212A.

Because processing circuitry 110 uses oxygen saturation prediction model 124 to predict whether oxygen saturation level 202 of patient 101 will increase above desaturation threshold 208 within time period 206 when oxygen saturation level 202 of patient 101 reaches desaturation threshold 208 at time t1, the point of time at which oxygen saturation level 202 of patient 101 reaches desaturation threshold 208 is referred to as prediction point 204. At prediction point 204, processing circuitry 110 may use information associated with patient 101 collected over time period 214 immediately preceding prediction point 204 as input in order to predict the oxygen saturation level 202 of patient 101 at the end of time period 206. For example, oxygen saturation prediction model 124 may receive one or more of: the oxygen saturation levels of patient 101, the blood pressure of patient 101, and/or one or more metrics derived from the PPG signals of patient 101 that are determined over time period 214 to predict the oxygen saturation level 202 of patient 101 at the end of time period 206.

If processing circuitry 110 predicts that oxygen saturation level 202 of patient 101 will not increase above desaturation threshold 208 by the end of time period 206, then processing circuitry 110 may output a notification indicative of patient 101 experiencing an oxygen desaturation event. On the other hand, if processing circuitry 110 predicts that oxygen saturation level 202 of patient 101 will increase above desaturation threshold 208 by the end of time period 206, then processing circuitry 110 may refrain from outputting a notification indicative of patient 101 experiencing an oxygen desaturation event. For example, processing circuitry 110 may refrain from outputting the notification at prediction point 204 to reduce the possibility of providing a nuisance notification, and may instead reevaluate whether a desaturation event is detected at the end of time period 206. In this way, processing circuitry 110 may confirm the desaturation event is present based on additional sensed oxygen saturation levels.

For example, in some examples, in response to predicting that oxygen saturation level 202 of patient 101 will increase above desaturation threshold 208 by the end of time period 206, processing circuitry 110 may continue to monitor the oxygen saturation level of patient 101 over time from prediction point 204 until the end of time period 206. At the end of time period 206 at time t3, processing circuitry 110 may determine whether oxygen saturation level 202 of patient 101 has increased above desaturation threshold 208. If processing circuitry 110 determines that oxygen saturation level 200 of patient 101 has not increased above desaturation threshold 208 by the end of time period 206, then processing circuitry 110 may output a notification indicative of patient 101 experiencing a desaturation event.

In some examples, processing circuitry 110 may output a notification (via user interface 130) prior to the end of time period 206 if one or more oxygen saturation conditions are detected. This may enable device 100 to provide relatively timely indications of one or more patient conditions for which it may be desirable to provide more immediate notifications, e.g., a desaturation event for which more immediate clinician intervention may be desirable. For example, in some examples, processing circuitry 110 may output a notification if the oxygen saturation level of patient 101 drops below deep desaturation threshold 210 prior to the end of time period 206. Deep desaturation threshold 210 is another oxygen saturation threshold value stored by memory 120 (FIG. 1) or another device and is indicative of an oxygen saturation level below desaturation threshold 208. For example, deep desaturation threshold 210 may be indicative of an oxygen saturation level for which more immediate clinician intervention is desired compared to desaturation threshold 208. In the example of FIG. 2, if processing circuitry 110 determines that the oxygen saturation level of patient 101 follows oxygen saturation curve 212C and decreases to reach deep desaturation threshold 210 at time t2, then processing circuitry 110 may, in response, output a notification indicative of patient 101 experiencing a deep oxygen desaturation event. In some examples, the notification indicative of a deep oxygen desaturation event may differ from a notification indicative of an oxygen desaturation event to better alert a clinician of the nature of the detected patient event. In other examples, the same notification may be used to indicate both the oxygen desaturation event and the deep oxygen desaturation event.

As another example, which can be used alone or in combination with the deep oxygen saturation threshold example discussed above, processing circuitry 110 may output a notification prior to the end of time period 206 if the oxygen saturation level of patient 101 continues to decrease after prediction point 204. For example, if processing circuitry 110 determines that the oxygen saturation level of patient 101 follows oxygen saturation curve 212A and decreases by a predetermined percentage (e.g., 5% or more) in a predetermined first part of time period 206 (e.g., the first 6 seconds of time period 206 that is 10 seconds), processing circuitry 110 may, in response, output a notification indicative of patient 101 experiencing an oxygen desaturation event without waiting for the end of time period 206.

In some examples, instead of predicting whether oxygen saturation level 202 of patient 101 will increase above desaturation threshold 208 by the end of time period 206, processing circuitry 110 may use oxygen saturation prediction model 124 to predict whether oxygen saturation level 202 of patient 101 will increase above a threshold that is different from desaturation threshold 208 by the end of time period 206. For example, when the oxygen saturation level of patient 101 decreases to reach desaturation threshold 208 at prediction point 204, processing circuitry 110 may use oxygen saturation prediction model 124 to predict whether oxygen saturation level 202 of patient 101 will increase above threshold 216 that is different from desaturation threshold 208. For example, desaturation threshold 208 may have a value 90% while threshold 216 may have a value of 92%, 88%, or another value different from the value of desaturation threshold 208.

In some examples, processing circuitry 110 may monitor the accuracy of predictions made using oxygen saturation prediction model 124. If processing circuitry 110 determines that the accuracy of predictions made using oxygen saturation prediction model 124 decreases below a set threshold (e.g., 70% accuracy), then processing circuitry 110 may refrain from relying on predictions made using oxygen saturation prediction model 124 to determine whether to delay the outputting of notifications indicative of patient 101 experiencing oxygen desaturation events. That is, when oxygen saturation level 202 of patient 101 decreases to reach desaturation threshold 208, processing circuitry 110 may, in response, output a notification indicative of patient 101 experiencing an oxygen desaturation event regardless of whether oxygen saturation prediction model 124 predicts that oxygen saturation level 202 of patient 101 will increase above desaturation threshold 208 by the end of time period 206. This may help processing circuitry 110 provide timely notifications of detected desaturation events.

In some examples, even when processing circuitry 110 refrains from relying on predictions made using oxygen saturation prediction model 124 to determine whether to delay the outputting of notifications indicative of patient 101 experiencing oxygen desaturation events, processing circuitry 110 may continue to use oxygen saturation prediction model 124 to determine whether to delay the outputting of notifications indicative of patient 101 experiencing oxygen desaturation events. This may enable processing circuitry 110 to begin using oxygen saturation prediction model 124 again. For example, when processing circuitry 110 determines that the accuracy of predictions made using oxygen saturation prediction model 124 has increased back above a set threshold, processing circuitry 110 may once again start relying on predictions made using oxygen saturation prediction model 124 to determine whether to delay the outputting of notifications indicative of patient 101 experiencing oxygen desaturation events.

In some examples, instead of predicting whether oxygen saturation level 202 of patient 101 will increase above desaturation threshold 208 by the end of time period 206, the techniques described herein may be equally applicable to predicting whether oxygen saturation level 202 of patient 101 will increase above a predetermined threshold, such as threshold 216, by the end of time period 206. For example, for neonates, an oxygen saturation level that is too high may be indicative of a medical event requiring clinician intervention. As such, when the oxygen saturation level 202 of a neonate patient, such as patient 101, increases from being below threshold 216 to reach threshold 216 at prediction point 204, processing circuitry 110 may use oxygen saturation prediction model 124 to predict whether the oxygen saturation level 202 of patient 101 will increase above threshold 216 by the end of time period 206.

If processing circuitry 110 predicts that the oxygen saturation level 202 of patient 101 will decrease below threshold 216 by the end of time period 206, then processing circuitry 110 may refrain from outputting a notification at prediction point 204. At the end of time period 206, processing circuitry 110 may determine whether the oxygen saturation level 202 of patient 101 has decreased below threshold 216. If processing circuitry 110 determines that the oxygen saturation level 202 of patient 101 has not decreased below threshold 216 at the end of time period 206, then processing circuitry 110 may output a notification indicative of a relatively high oxygen saturation level, e.g., the oxygen saturation level 202 of patient 101 being at or above threshold 216.

Figure 3:
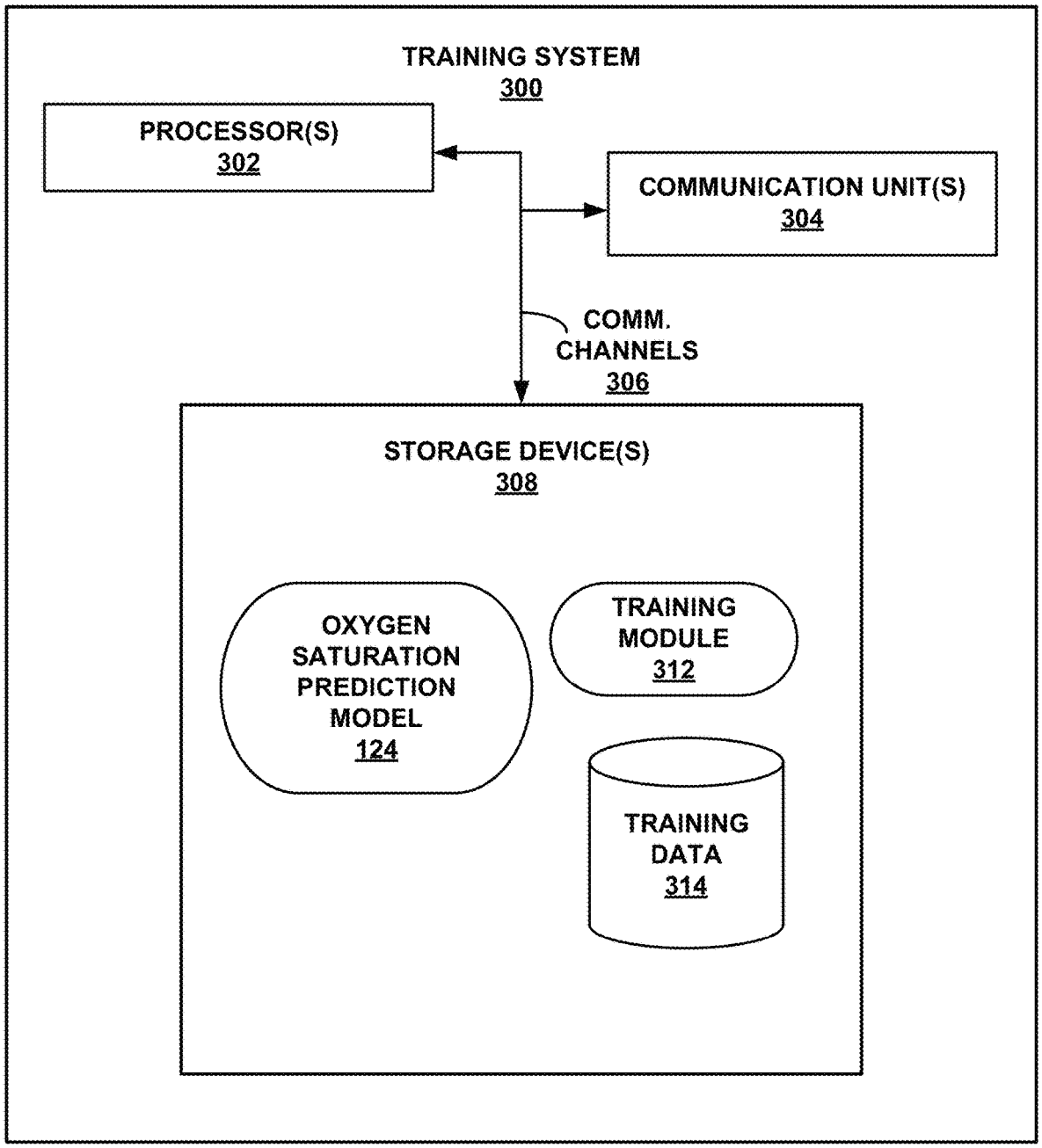
FIG. 3 illustrates details of an example training system that may perform training of oxygen saturation prediction model shown in FIG. 1.

FIG. 3 illustrates details of an example training system 300 that may perform training of oxygen saturation prediction model 124 shown in FIG. 1. FIG. 3 illustrates only one particular example of training system 300, and many other example devices having more, fewer, or different components may also be configurable to perform operations in accordance with techniques of the present disclosure.

While displayed as part of a single device in the example of FIG. 3, components of training system 300 may, in some examples, be located within and/or be a part of different devices. For instance, in some examples, training system 300 may represent a "cloud" computing system. Thus, in these examples, the modules illustrated in FIG. 3 may span across multiple computing devices. In some examples, training system 300 may represent one of a plurality of servers making up a server cluster for a "cloud" computing system.

In other examples, training system 300 may be an example of oxygen saturation monitoring device 100 shown in FIG. 1.

As shown in the example of FIG. 3, training system 300 includes one or more processors 302 (which may also be referred to as processing circuitry), one or more communications units 304, and one or more storage devices 308. Storage devices 308 further include oxygen saturation prediction model 124, training module 312, and training data 314. Each of components 302, 304, and 308 may be interconnected (physically, communicatively, and/or operatively) for inter-component communications. In the example of FIG. 3, components 302, 304, and 308 may be coupled by one or more communications channels 306. In some examples, communications channels 306 may include a system bus, network connection, inter-process communication data structure, or any other channel for communicating data. Oxygen saturation prediction model 124, training module 312, and training data 314 may also communicate information with one another as well as with other components in training system 300.

In the example of FIG. 2, one or more processors 302 may implement functionality and/or execute instructions within training system 300. For example, one or more processors 302 may receive and execute instructions stored by storage devices 308 that execute the functionality of training module 312. These instructions executed by one or more processors 302 may cause training system 300 to store information within storage devices 308 during execution. One or more processors 302 may execute instructions of training module 312 to train oxygen saturation prediction model 124 using training data 314. That is, training module 312 may be operable by one or more processors 302 to perform various actions or functions of training system 300 described herein.

In the example of FIG. 3, one or more communication units 304 may be operable to communicate with external devices via one or more networks by transmitting and/or receiving network signals on the one or more networks. For example, training system 300 may use communication units 304 to transmit and/or receive radio signals on a radio network such as a cellular radio network. Likewise, communication units 304 may transmit and/or receive satellite signals on a satellite network such as a global positioning system (GPS) network. Examples of communication units 304 include a network interface card (e.g. such as an Ethernet card), an optical transceiver, a radio frequency transceiver, or any other type of device that can send and/or receive information. Other examples of communication units 304 may include Near-Field Communications (NFC) units, Bluetooth® radios, short wave radios, cellular data radios, wireless network (e.g., Wi-Fi®) radios, as well as universal serial bus (USB) controllers.

One or more storage devices 308 may be operable, in the example of FIG. 3, to store information for processing during operation of training system 300. In some examples, storage devices 308 may represent temporary memory, meaning that a primary purpose of storage devices 308 is not long-term storage. For instance, storage devices 308 of training system 300 may be volatile memory, configured for short-term storage of information, and therefore not retain stored contents if powered off. Examples of volatile memories include random access memories (RAM), dynamic random access memories (DRAM), static random access memories (SRAM), and other forms of volatile memories known in the art.

Storage devices 308, in some examples, also represent one or more computer-readable storage media. That is, storage devices 308 may be configured to store larger amounts of information than a temporary memory. For instance, storage devices 308 may include non-volatile memory that retains information through power on/off cycles. Examples of non-volatile memories include magnetic hard discs, optical discs, floppy discs, flash memories, or forms of electrically programmable memories (EPROM) or electrically erasable and programmable (EEPROM) memories. In any case, storage devices 308 may, in the example of FIG. 3, store program instructions and/or data associated with oxygen saturation prediction model 124, training module 312, and training data 314.

Training system 300 may, in the example of FIG. 3, execute training module 312 to train oxygen saturation prediction model 124 using training data 314 to more accurately predict whether the oxygen saturation level of a patient will rise above a desaturation threshold (or, in other examples, decrease to at or below a high saturation threshold) at the end of a predefined time period. For example, training system 300 may train oxygen saturation prediction model 124 to associate one or more of: a history of the oxygen saturation levels of the patient over a time period immediate preceding the prediction point, the history of blood pressure values of the patient over the time period, and/or one or more metrics derived from the PPG signals of the patient that are determined over the time period. Oxygen saturation prediction model 124 may include a deep learning architecture such as a recurrent neural network, convolutional neural network, and the like that includes multiple layers to progressively extract higher level features from inputs to oxygen saturation prediction model 124.

In some examples, training data 314 used to train oxygen saturation prediction model 124 includes data from only patient 101 and from no other subjects. For example, training system 300 may receive sets of one or more of: the history of oxygen saturation levels of patient 101, the history of blood pressure values of patient 101, and/or one or more metrics derived from the PPG signals of patient 101 that are determined over time periods immediately prior to prediction points and corresponding sets of oxygen saturation levels of patient 101 at the end of the predefined time period in order to associate the sets of input features with the corresponding oxygen saturation levels of patient 101 at the end of the predefined time period.

In other examples, training data 314 may include data from a population of patients, such as sets of one or more of: the oxygen saturation levels of the population of patients, the blood pressure of the population of patients, and/or one or more metrics derived from the PPG signals of the population points that are determined over a time period prior to prediction points and corresponding sets of oxygen saturation levels of patient 101 at the end of the predefined time period and corresponding sets of oxygen saturation levels of the population of patients at the end of the predefined time period in order to associate the sets of input features with the corresponding oxygen saturation levels of the population of patients at the end of the predefined time period.

In some examples, once training module 312 has trained oxygen saturation prediction model 124 using training data 314, training module 312 may test oxygen saturation prediction model 124 by using a set of test data not yet encountered by oxygen saturation prediction model 124 to determine how closely the oxygen saturation levels predicted by oxygen saturation prediction model 124 matches the expected target oxygen saturation levels of the test data. In this way, training module 312 may evaluate and further refine oxygen saturation prediction model 124.

When training module 312 has completed training of oxygen saturation prediction model 124, oxygen saturation prediction model 124 can be installed, uploaded, or otherwise transferred to oxygen saturation monitoring device 100. In some examples, training module 312 may upload or otherwise transfer a copy of oxygen saturation prediction model 124 to another server or to the cloud, and oxygen saturation monitoring device 100 may use oxygen saturation prediction model 124 via a network such as the Internet, a virtual private network, a local area network, and the like.

In some examples, oxygen saturation monitoring device 100 uses oxygen saturation prediction model 124 to predict the oxygen saturation level of a patient, such as patient 101, processing circuitry 110 of oxygen saturation monitoring device 100 or other processing circuitry may calibrate oxygen saturation prediction model 124 based on a history of accuracy of oxygen saturation prediction model 124. Processing circuitry 110 may, for example, determine offsets between the oxygen saturation levels of patient 101 at the end of predefined time periods predicted using oxygen saturation prediction model 124 and the actual oxygen saturation levels of patient 101 at the end of predefined time periods, and may determine a linear offset that is applied to the oxygen saturation levels of patient 101 predicted using oxygen saturation prediction model 124.

For example, processing circuitry 110 of oxygen saturation monitoring device 100 may determine an average of the offsets between the oxygen saturation levels of patient 101 at the end of predefined time periods predicted using oxygen saturation prediction model 124 and the actual oxygen saturation levels of patient 101 at the end of predefined time periods and may add or subtract the average of the offsets to the oxygen saturation levels of patient 101 predicted using oxygen saturation prediction model 124 in order to calibrate the oxygen saturation levels of patient 101 predicted using oxygen saturation prediction model 124.

In another example, processing circuitry 110 may determine, for each of a range of oxygen saturation levels of patient 101 predicted using oxygen saturation prediction model 124, determine a corresponding offset between the predicted oxygen saturation level and the actual oxygen saturation level, in order to determine different offsets for each of a range of oxygen saturation levels of patient 101 predicted using oxygen saturation prediction model 124. Oxygen saturation monitoring device 100 may store such an offset or such a set of offsets in memory 120, such as in the form of a lookup table, for calibrating oxygen saturation prediction model 124.

In some examples, training system 314 and/or oxygen saturation monitoring device 100 may retrain oxygen saturation prediction model 124, such as by performing a transfer learning cycle to update the weights in oxygen saturation prediction model 124 to better suit specific patients (e.g., patient 101). Oxygen saturation monitoring device 100 may, for a patient such as patient 101, store the input features for oxygen saturation prediction model 124 and the corresponding oxygen saturation level of patient 101 at the end of the predefined time period each time oxygen saturation monitoring device executes oxygen saturation prediction model 124 to predict the oxygen saturation level of patient 101 at the end of the predefined time period. Once oxygen saturation monitoring device 100 has collected enough data to perform such retraining, training system 314 and/or oxygen saturation monitoring device 100 may retrain oxygen saturation prediction model 124 using such stored sets of input features and corresponding oxygen saturation levels of patient 101 at the end of the predefined time period to personalize oxygen saturation prediction model 124 for patient 101. For example, training system 214 and/or oxygen saturation monitoring device 100 may perform a short retraining of the neural network of oxygen saturation prediction model 124 with a lower learning rate and/or with many of the weights in the early layers in the neural network frozen based on the data collected from patient 101 in order to personalize oxygen saturation prediction model 124 for patient 101.

Figure 4:
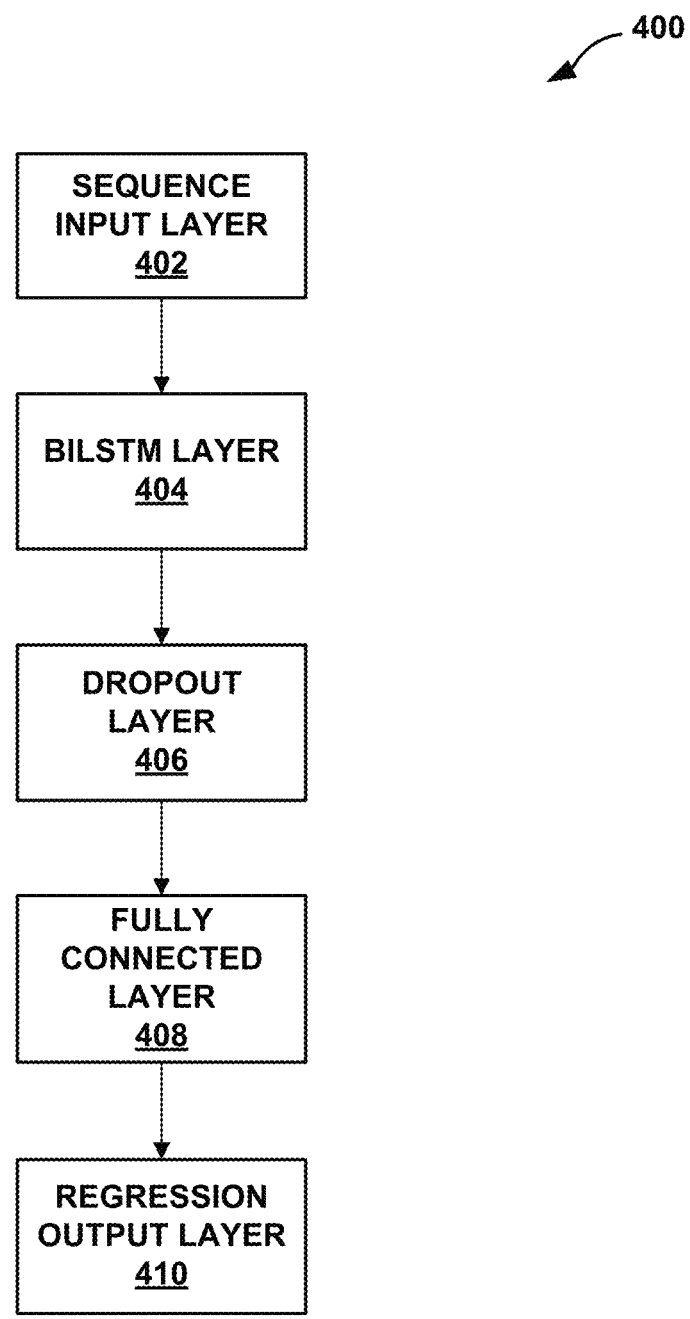
FIG. 4 illustrates an example deep learning architecture of the oxygen saturation prediction model of FIG. 1.

FIG. 4 illustrates an example deep learning architecture 400 of the oxygen saturation prediction model 124 of FIG. 1. While deep learning architecture 400 is illustrated in FIG. 4 as being a long short-term memory (LSTM) deep learning architecture that is used to train a LSTM model, any other deep learning architectures, such as a convolutional neural network (CNN) may equally be suitable for training oxygen saturation prediction model 124.

As shown in FIG. 4, deep learning architecture 400 may include sequence input layer 402, bidirectional long short-term memory (BiLSTM) layer 404, dropout layer 406, fully connected layer 408, and regression output layer 410. Sequence input layer 402 may be connected to BiLSTM layer 404. BiLSTM layer 404 may be connected to dropout layer 406. Dropout layer 406 may be connected to fully connected layer 408. Fully connected layer 408 may be connected to regression output layer 410.

A sequence input layer such as sequence input layer 402 inputs sequence data to a neural network. Thus, sequence input layer 402 receives features that are used to train deep learning architecture 400. To train oxygen saturation prediction model 124, sequence input layer 402 may receive features for patient 102 or for a population of patients, which include values of one or more of: the oxygen saturation levels of the population of patients, the blood pressures of the population of patients, and/or one or more metrics derived from the PPG signals of the population of patients that are determined during a time period immediately preceding the prediction point. The metrics derived from the PPG signals may include any combination of metrics, such as one or more of a skew of PPG pulses, PPG pulse amplitudes, normalized amplitudes of PPG pulses, PPG pulse maximum slope, the location of the PPG pulse maximum slope, PPG pulse maximum curvature, the location of the PPG pulse maximum curvature, or any other suitable morphological parameters derived from the PPG signals.

A BiLSTM layer such as BiLSTM layer 404 learns bidirectional long-term dependencies between time steps of time series or sequence data. These dependencies may be useful for the network to learn from a complete time series at each time step.

A dropout layer such as dropout layer 406 randomly sets input elements to zero with a given probability. By randomly setting input elements to zero, a dropout layer may enable elements to be ignored during the training phase. Selectively ignoring elements during the training phase may prevent over-fitting of training data.

A fully connected layer such as fully connected layer 408 multiplies the input (e.g., from dropout layer 406) by a weight matrix and then adds a bias vector. A regression output layer such as regression output layer 410 computes the half-mean-squared-error loss, or any other loss metric, for regression problems and outputs a predicted response of the trained regression network as a result of training oxygen saturation prediction model 124 having deep learning architecture 400.

To train oxygen saturation prediction model 124 having deep learning architecture 400, training system 300 (FIG. 3)

may derive a set of features and associated target values and may input the features and the associated target values into oxygen saturation prediction model 124 to train oxygen saturation prediction model 124 to estimate target values based on the inputted features. For example, to train oxygen saturation prediction model 124 to predict the oxygen saturation level of patient 101 by the end of a predefined time period, training system 300 may extract features from one or more of: the history oxygen saturation levels of patient 101 during a time period immediately preceding the prediction point, the history of blood pressure values of patient 101 during the time period immediately preceding the prediction point, and/or one or more metrics derived from the PPG signals of patient 101 during the time period immediately preceding the prediction point, and may use such extracted features associated with target predicted oxygen saturation levels at the end of predefined time periods to train oxygen saturation prediction model 124 to predict the future oxygen saturation levels of patient 101 from such features.

While training of deep learning architecture 400 of oxygen saturation prediction model 124 is described herein as a regression problem for predicting a single continuous variable (i.e., the future oxygen saturation level of a patient), oxygen saturation prediction model 124 may not necessarily be limited to a regression model. In other examples, the training of deep learning architecture 400 of oxygen saturation prediction model 124 may be similarly formulated as a classification problem, such as classifying the future oxygen saturation level of a patient, or as any other suitable problem.

Figure 5:
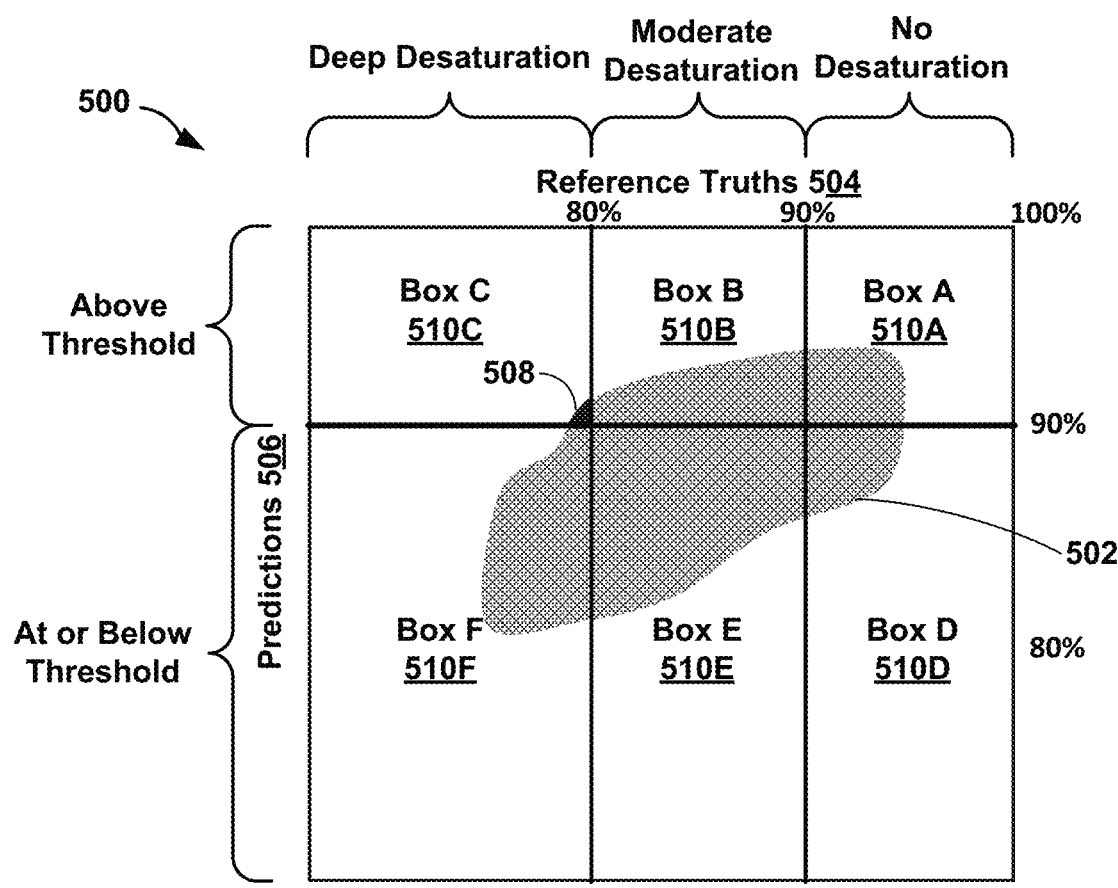
FIG. 5 illustrates an example spread of prediction points versus the reference truth of predictions made using the example oxygen saturation prediction model of FIG. 1.

FIG. 5 illustrates an example spread of prediction points versus the reference truth of predictions made using example oxygen saturation prediction model 124 of FIG. 1. As shown in FIG. 5, graph 500 include prediction points 502, which are oxygen saturation levels at the end of a predefined time period predicted using oxygen saturation prediction model 124, plotted against reference truths 504 and predictions 506, where reference truths 504 are the actual oxygen saturation levels of patients (sensed by oxygen saturation sensors, such as sensor 150 of FIG. 1) at the end of the predefined time period and predictions 506 are the predicted oxygen saturation levels of the patients at the end of the predefined time period.

Box A 510A, box B 510B, and box C 510C are boxes where processing circuitry 110 of oxygen saturation monitoring device 100 predicts that the oxygen saturation levels of one or more patients will increase above the desaturation threshold by the end of a predefined time period, and therefore refrains from outputting notifications indicative of oxygen desaturation events. Box A 510A is also a box where the actual oxygen saturation levels of one or more patients do increase above the desaturation threshold by the end of a predefined time period. As such, prediction points 502 in box A 510A are accurate oxygen saturation level predictions made by processing circuitry 110.

Box B 510B is also a box where the actual oxygen saturation levels of the one or more patients do not increase above the desaturation threshold by the end of a predefined time period. As such, prediction points 502 in box B 510B are not accurate predictions of oxygen saturation levels, and processing circuitry 110 may incorrectly refrain from outputting a notification until the end of the predefined time period. However, because box B 510B is associated with one or more patients experiencing moderate oxygen desaturation (e.g., an oxygen saturation level between a desaturation threshold and a deep desaturation threshold, such as between 80%-90%) for a relatively short period of time (e.g., 10 seconds) before processing circuitry 110 outputs a notifications indicative of oxygen desaturation events, such an error in the predictions made by processing circuitry 110 may be deemed acceptable.

Box C 510C is also a box where the actual oxygen saturation levels of one or more patients decrease below a deep desaturation threshold by the end of a predefined time period. As such, the portion 508 of prediction points 502 in box B 510B are not accurate predictions of oxygen saturation levels, and processing circuitry 110 may incorrectly delay outputting a notification until the end of the predefined time period. While oxygen saturation monitoring device 100 may still output a notification at the end of the predefined time period, aspects of the present disclosure includes training oxygen saturation prediction model 124 to minimize the prediction points that are in box C 510C and to minimize delays in outputting notifications for patients that experience deep desaturation events, as such deep desaturation events may be indicative of medical issues for which it may be desirable for a clinician to address in a timely manner.

Box D 510D, box E 510E, and box F 510F are boxes where processing circuitry 110 predicts that the oxygen saturation level of one or more patients will not increase above the desaturation threshold by the end of a predefined time period. As such, processing circuitry 110 may output notifications at the prediction point that are indicative of patients experiencing oxygen desaturation events.

Box D 510D is also a box where the actual oxygen saturation levels of the one or more patients do increase above the desaturation threshold by the end of a predefined time period. As such, prediction points 502 in box D 510D are not accurate predictions of oxygen saturation levels, and processing circuitry 110 may output notifications at the prediction point that are indicative of oxygen desaturation events.

Box E 510E and box F 510F are also boxes where the actual oxygen saturation levels of the one or more patients remains below the desaturation threshold by the end of a predefined time period. As such, prediction points 502 in box E 510E and box F 510F are accurate predictions of oxygen saturation levels, and processing circuitry 110 correctly outputs notifications at the prediction point that are indicative of oxygen desaturation events.

As shown in the example of FIG. 5, because portion 508 of prediction points 502 that are in box C 510C represent deep desaturation events that are incorrectly predicted by oxygen saturation prediction model 124, training system 300 and/or oxygen saturation monitoring device 100 may train oxygen saturation prediction model 124 to minimize portion 508 of prediction points 502 that are in box C 510C, thereby minimizing delays in outputting a notification for deep desaturation events. Similarly, training system 300 and/or oxygen saturation monitoring device 100 may also train oxygen saturation prediction model 124 to minimize the prediction points that are in box B 510B and box D 510D as much as possible in favor of prediction points in box A 510A, box E 510E, and box F 510F, as described in further detail below.

Figure 6:
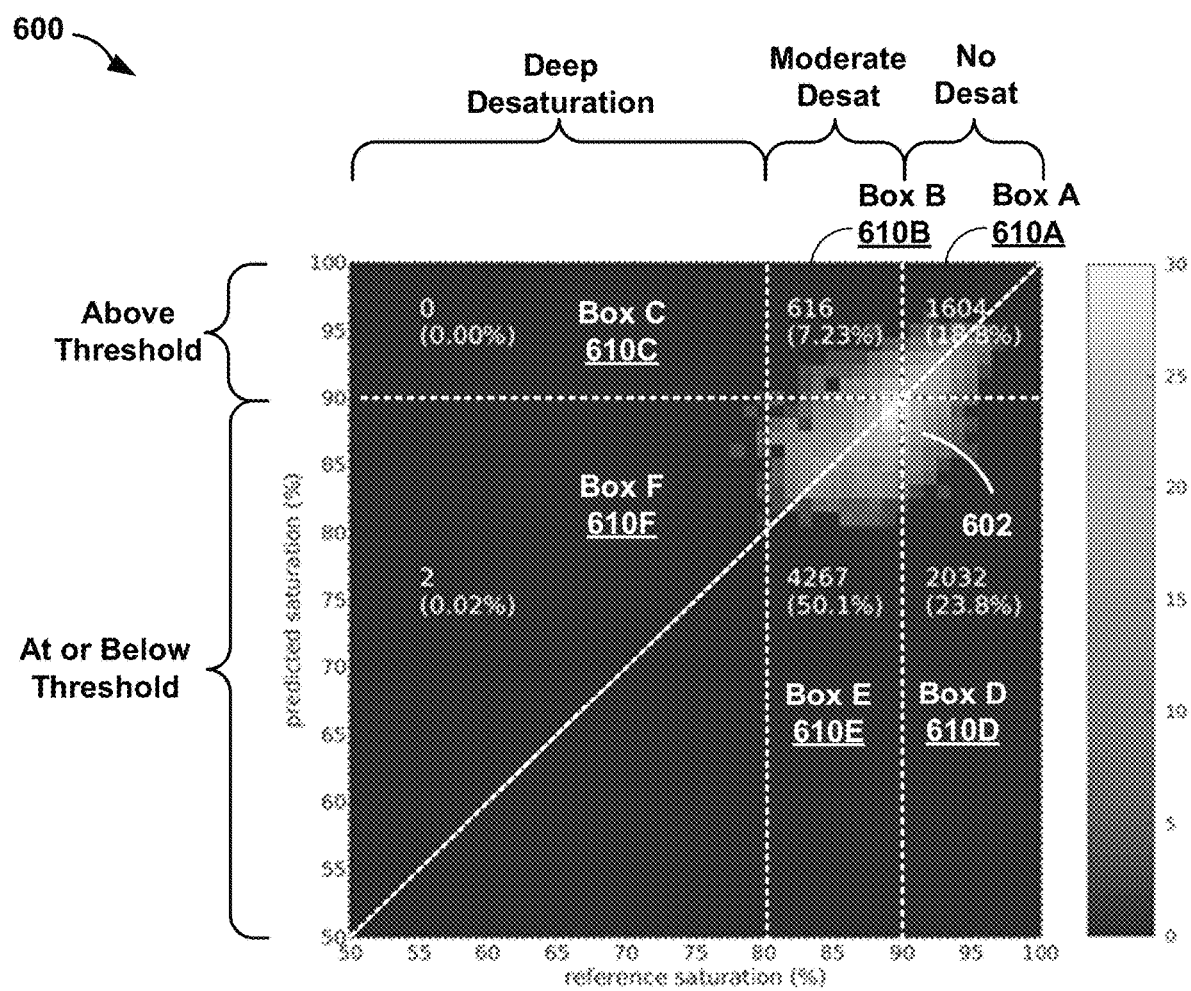
FIG. 6 illustrates a spread of prediction points versus the reference truth of predictions made using the example oxygen saturation prediction model of FIG. 1 over an example sample set of data.

FIG. 6 illustrates an example spread of prediction points versus the reference truth of predictions made using the example oxygen saturation prediction model 124 shown in FIG. 1 over a sample set of data. As shown in FIG. 6, graph 600 is a density plot of prediction points collected from approximately 1200 patients, with most of the patients experiencing multiple desaturations, and excluding data collected while patients were in motion.

In graph 600, the desaturation threshold is 90%, the deep desaturation threshold in graph 600 is 80%, and the predefined time period is 10 seconds. Thus, a patient having (sensed) oxygen saturation levels above 90% is indicative of the patient not experiencing desaturation, a patient having (sensed) oxygen saturation levels between 80% and 90% is indicative of the patient experiencing moderate desaturation, and a patient having (sensed) oxygen saturation levels below 80% is indicative of the patient experiencing deep desaturation. Prediction points 602 are clustered around 90% reference oxygen saturation and 90% predicted oxygen saturation, which may be expected because the oxygen saturation level of the patient is at 90% at the beginning of the prediction period.

Similar to graph 500 of FIG. 5, graph 600 includes box A 610A, box B 610B, box C 610C, box D 610D, box E 610E, and box F 610F, and training system 300 may train oxygen saturation prediction model 124 to minimize the amount of prediction points 602 in box C 610C while reducing the amount of prediction points in box B 610B and box D 610D in favor of prediction points 602 in box A 610A, box E 610E, and box F 610F.

The following table lists the number of prediction points 602 in each of box A 610A, box B 610B, box C 610C, box D 610D, box E 610E, and box F 610F in graph 600:

| Box | Number of Prediction Points |
|---|---|
| A | 1,604 |
| B | 616 |
| C | 0 |
| D | 2,032 |
| E | 4,267 |
| F | 2 |
| Total | 8,521 |

As can be seen in the table, the number of prediction points 602 in box C 610C is 0. As such, the use of oxygen saturation prediction model 124 to generate prediction points 602 in the example of FIG. 6 did not miss any deep desaturation events. As can also be seen, the number of prediction points 602 in box A 610A, box B 610B, and box C 610C sum up to 2,220 prediction points. As such, in the example of FIG. 6, the use of oxygen saturation prediction model 124 to generate prediction points 602 may reduce the number of times oxygen saturation monitoring device 100 outputs a notification by 1604, which is about 18.8% of the total number of prediction points.

Figure 7:
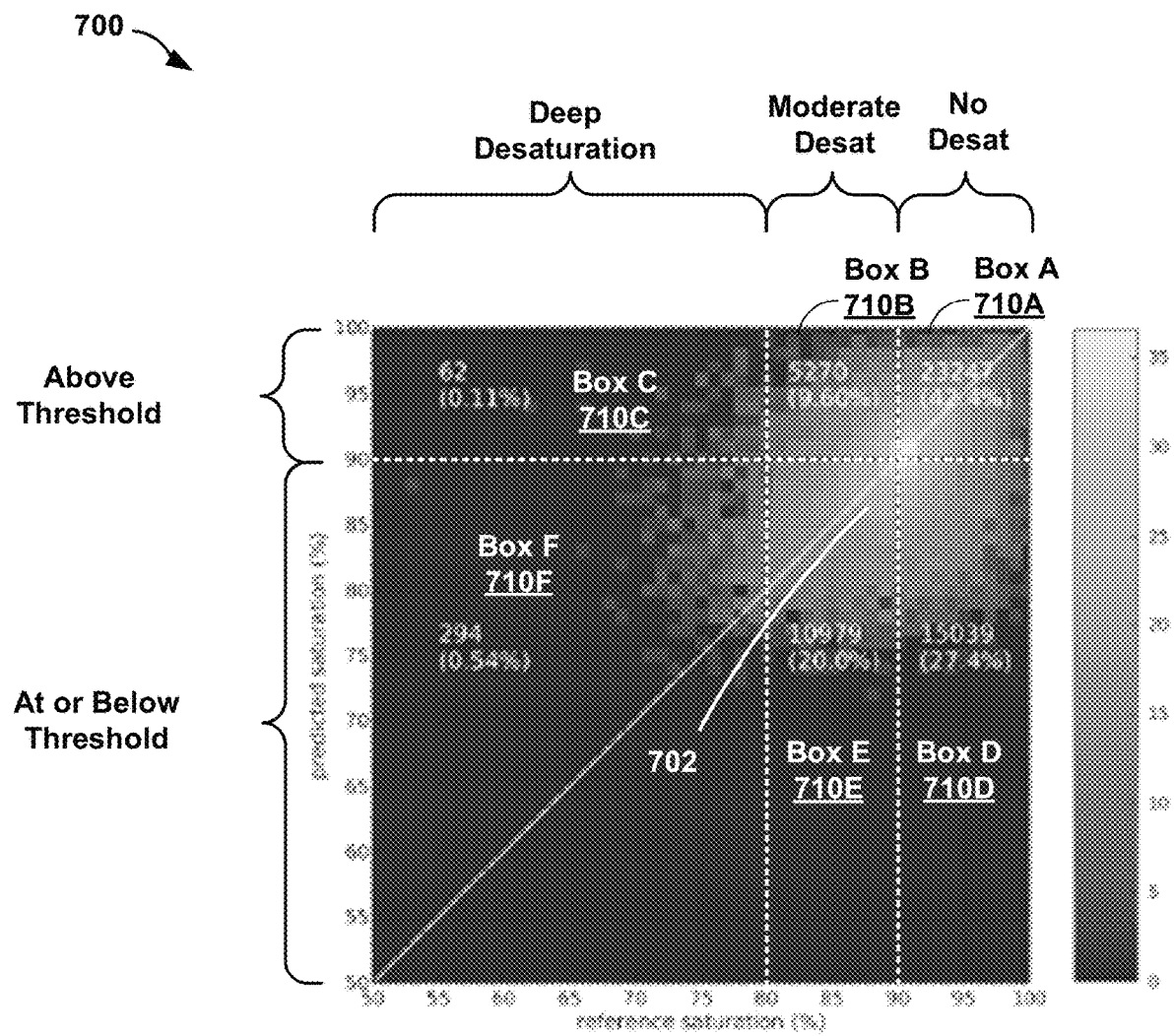
FIG. 7 illustrates a spread of prediction points versus the reference truth of predictions made using the example oxygen saturation prediction model of FIG. 1 over an example sample set of data.

FIG. 7 illustrates an example spread of prediction points versus the reference truth of predictions made using the example oxygen saturation prediction model 124 of FIG. 1 over a sample set of data. FIG. 7 illustrates similar sample data as illustrated in FIG. 5 but without excluding data collected while patients were in motion.

As shown in FIG. 7, graph 700 is a density plot of prediction points collected from approximately 1200 patients, with most of the patients experiencing multiple desaturations. In graph 700, the desaturation threshold is 90%, the deep desaturation threshold in graph 700 is 80%, and the predefined time period is 10 seconds. Thus, a patient having (sensed) oxygen saturation levels above 90% is indicative of the patient not experiencing desaturation, a patient having (sensed) oxygen saturation levels between 80% and 90% is indicative of the patient experiencing moderate desaturation, and a patient having (sensed) oxygen saturation levels below 80% is indicative of the patient experiencing deep desaturation. Prediction points 702 are clustered around 90% reference oxygen saturation and 90% predicted oxygen saturation, which may be expected because the oxygen saturation level of the patient is at 90% at the beginning of the prediction period.

Similar to graph 600 of FIG. 6, graph 700 includes box A 710A, box B 710B, box C 710C, box D 710D, box E 710E, and box F 710F, where oxygen saturation prediction model 124 is trained to minimize the amount of prediction points 702 in box C 710C while reducing the amount of prediction points in box B 710B and box D 710D in favor of prediction points 702 in box A 710A, box E 710E, and box F 710F.

The following table lists the number of prediction points 702 in each of box A 710A, box B 710B, box C 710C, box D 710D, box E 710E, and box F 710F in graph 700:

| Box | Number of Prediction Points |
|---|---|
| A | 23,247 |
| B | 5,270 |
| C | 62 |
| D | 15,039 |
| E | 10,979 |
| F | 294 |
| Total | 54,981 |

As can also be seen, the number of prediction points 702 in box A 710A is 23,247 prediction points. As such, in the example of FIG. 7, the use of oxygen saturation prediction model 124 to generate prediction points 702 may reduce the number of times oxygen saturation monitoring device 100 outputs a notification by 23,247, which is about 42% of the total number of prediction points.

As can also be seen in the table, the number of prediction points 702 in box C 710C is 64 while the number of prediction points 702 in box F 710F is 294. As such, the use of oxygen saturation prediction model 124 to generate prediction points 702 in the example of FIG. 6 correctly predicted 294 deep desaturation events and missed 62 deep desaturation events.

In some aspects of the present disclosure, training system 300 and/or processing circuitry 110 of oxygen saturation monitoring device 100 may retrain oxygen saturation prediction model 124, such as by using different hyperparameters, to minimize incorrect predictions made using oxygen saturation prediction model 124 of blood oxygen levels of patients (e.g., patient 101) that miss deep oxygen desaturation events experienced by patient 101. For example, training system 300 and/or oxygen saturation monitoring device 100 may retrain oxygen saturation prediction model 124 using a loss function to minimize (i.e., reduce) the number of missed deep desaturation events, such as by minimizing the number of prediction points 702 in box C 710C. One example of such a loss function is as follows:

$$L = (w \times N_C + (1-w)(N_B + N_D))/(N_{Total}),$$

where $N_{Total}$ is the total number of prediction points, $N_B$ is the number of prediction points in box B, $N_C$ is the number of prediction points in box C, $N_D$ is the number of prediction points in box D, and w is a weight that may range from 0 to 1. If w is 1, then only the number of prediction points in box C is minimized, while if w is 0, then the number of prediction points in box B and box D are minimized without minimizing the number of prediction points in box C. Training system 300 and/or oxygen saturation monitoring device 100 may determine a value for w to retrain oxygen saturation prediction model 124 based on the loss function to minimize one or more of $N_C$, $N_B$, and $N_D$.

Figure 8:
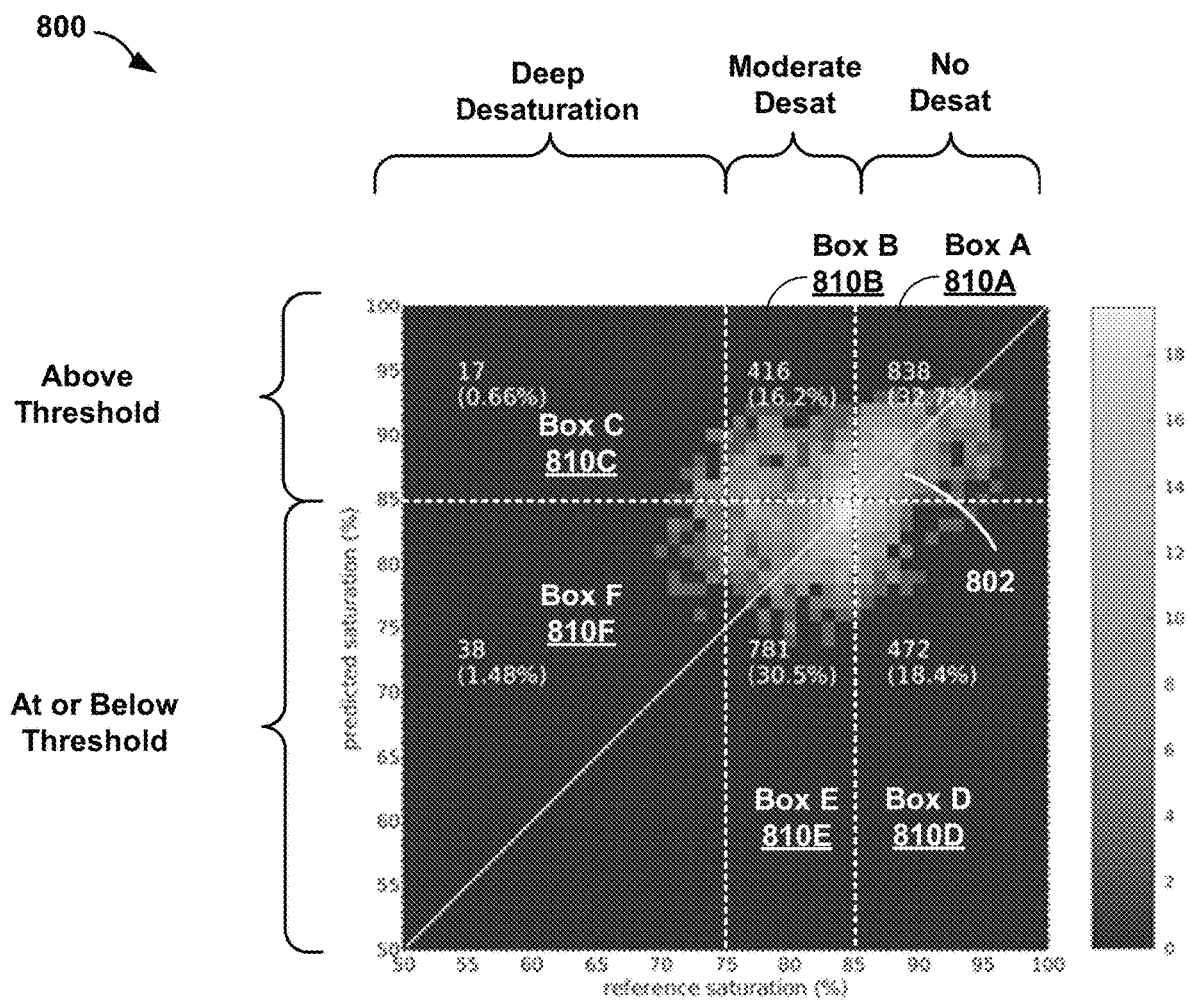
FIG. 8 illustrates a spread of prediction points versus the reference truth of predictions made using the example oxygen saturation prediction model of FIG. 1 over an example sample set of data.

FIG. 8 illustrates an example spread of prediction points versus the reference truth of predictions made using the example oxygen saturation prediction model 124 of FIG. 1 over a sample set of data. As shown in FIG. 8, graph 800 is a density plot of prediction points 806 collected from approximately 1200 patients, with most of the patients experiencing multiple desaturations, and excluding data collected while patients were in motion.

The desaturation threshold in graph 800 is 85%, while the deep desaturation threshold in graph 800 is 75%, and the predefined time period is 10 seconds. Thus, a patient having (sensed) oxygen saturation levels above 85% is indicative of the patient not experiencing desaturation, a patient having (sensed) oxygen saturation levels between 70% and 85% is indicative of the patient experiencing moderate desaturation, and a patient having (sensed) oxygen saturation levels below 70% is indicative of the patient experiencing deep desaturation Similar to graph 500 of FIG. 5, graph 800 includes box A 810A, box B 810B, box C 810C, box D 810D, box E 810E, and box F 810F, where oxygen saturation prediction model 124 is trained to minimize the amount of prediction points 802 in box C 810C while reducing the amount of prediction points in box B 810B and box D 810D in favor of prediction points 802 in box A 810A, box E 810E, and box F 810F.

The following table lists the number of prediction points 802 in each of box A 810A, box B 810B, box C 810C, box D 810D, box E 810E, and box F 810F in graph 800:

| Box | Number of Prediction Points |
| --- | --- |
| A | 838 |
| B | 416 |
| C | 17 |
| D | 472 |
| E | 781 |
| F | 38 |
| Total | 2,562 |

As can also be seen, the number of prediction points 802 in box A 810A is 838 prediction points. As such, in the example of FIG. 8, the use of oxygen saturation prediction model 124 to generate prediction points 802 may reduce the number of times oxygen saturation monitoring device 100 outputs a notification by 838, which is about 32.7% of the total number of prediction points.

As can also be seen in the table, the number of prediction points 802 in box C 810C is 17 while the number of prediction points 802 in box F 810F is 38. As such, the use of oxygen saturation prediction model 124 to generate prediction points 802 in the example of FIG. 8 correctly predicted 38 deep desaturation events and missed 17 deep desaturation events.

Figure 9:
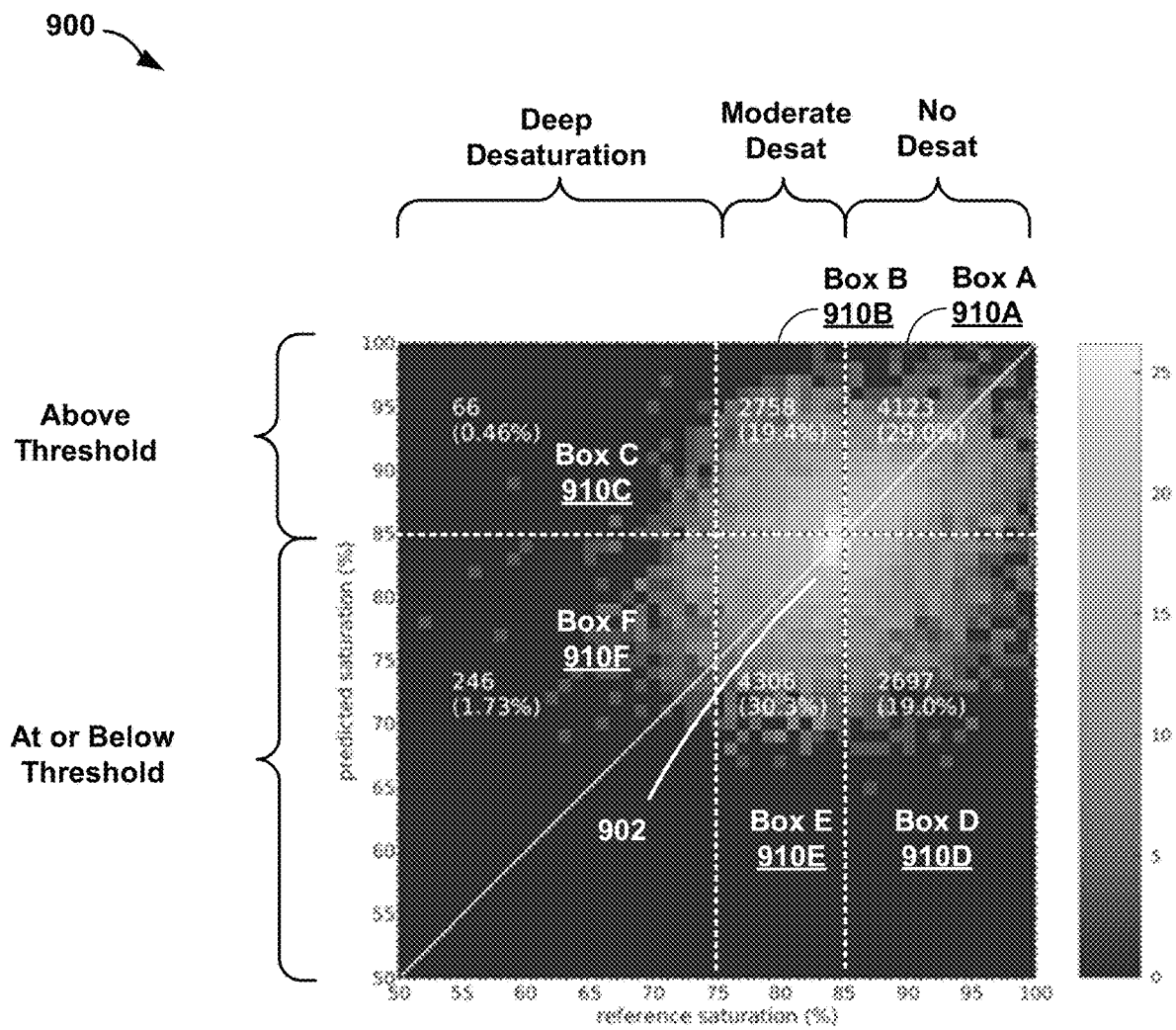
FIG. 9 illustrates a spread of prediction points versus the reference truth of predictions made using the example oxygen saturation prediction model of FIG. 1 over an example sample set of data.

FIG. 9 illustrates an example spread of prediction points versus the reference truth of predictions made using the example oxygen saturation prediction model 124 of FIG. 1 over a sample set of data. FIG. 9 illustrates similar sample data as illustrated in FIG. 8 but without excluding data collected while patients were in motion.

The desaturation threshold in graph 900 is 85%, while the deep desaturation threshold in graph 800 is 75%, and the predefined time period is 10 seconds. Thus, a patient having (sensed) oxygen saturation levels above 85% is indicative of the patient not experiencing desaturation, a patient having (sensed) oxygen saturation levels between 75% and 85% is indicative of the patient experiencing moderate desaturation, and a patient having (sensed) oxygen saturation levels below 75% is indicative of the patient experiencing deep desaturation Similar to graph 500 of FIG. 5, graph 900 includes box A 910A, box B 910B, box C 910C, box D 910D, box E 910E, and box F 910F, where oxygen saturation prediction model 124 is trained to minimize the amount of prediction points 902 in box C 910C while reducing the amount of prediction points in box B 910B and box D 910D in favor of prediction points 902 in box A 910A, box E 910E, and box F 910F.

The following table lists the number of prediction points 902 in each of box A 910A, box B 910B, box C 910C, box D 910D, box E 910E, and box F 910F in graph 900:

| Box | Number of Prediction Points |
| --- | --- |
| A | 4,123 |
| B | 2,758 |
| C | 66 |
| D | 2,697 |
| E | 4,306 |
| F | 246 |
| Total | 14,196 |

As can also be seen, the number of prediction points 902 in box A 910A is 4,123 prediction points. As such, in the example of FIG. 9, the use of oxygen saturation prediction model 124 to generate prediction points 902 may reduce the number of times oxygen saturation monitoring device 100 outputs a notification by 4,123, which is about 29% of the total number of prediction points.

As can also be seen in the table, the number of prediction points 902 in box C 910C is 66 while the number of prediction points 902 in box F 910F is 246. As such, the use of oxygen saturation prediction model 124 to generate prediction points 902 in the example of FIG. 6 correctly predicted 246 deep desaturation events and missed 66 deep desaturation events.

Figure 10:
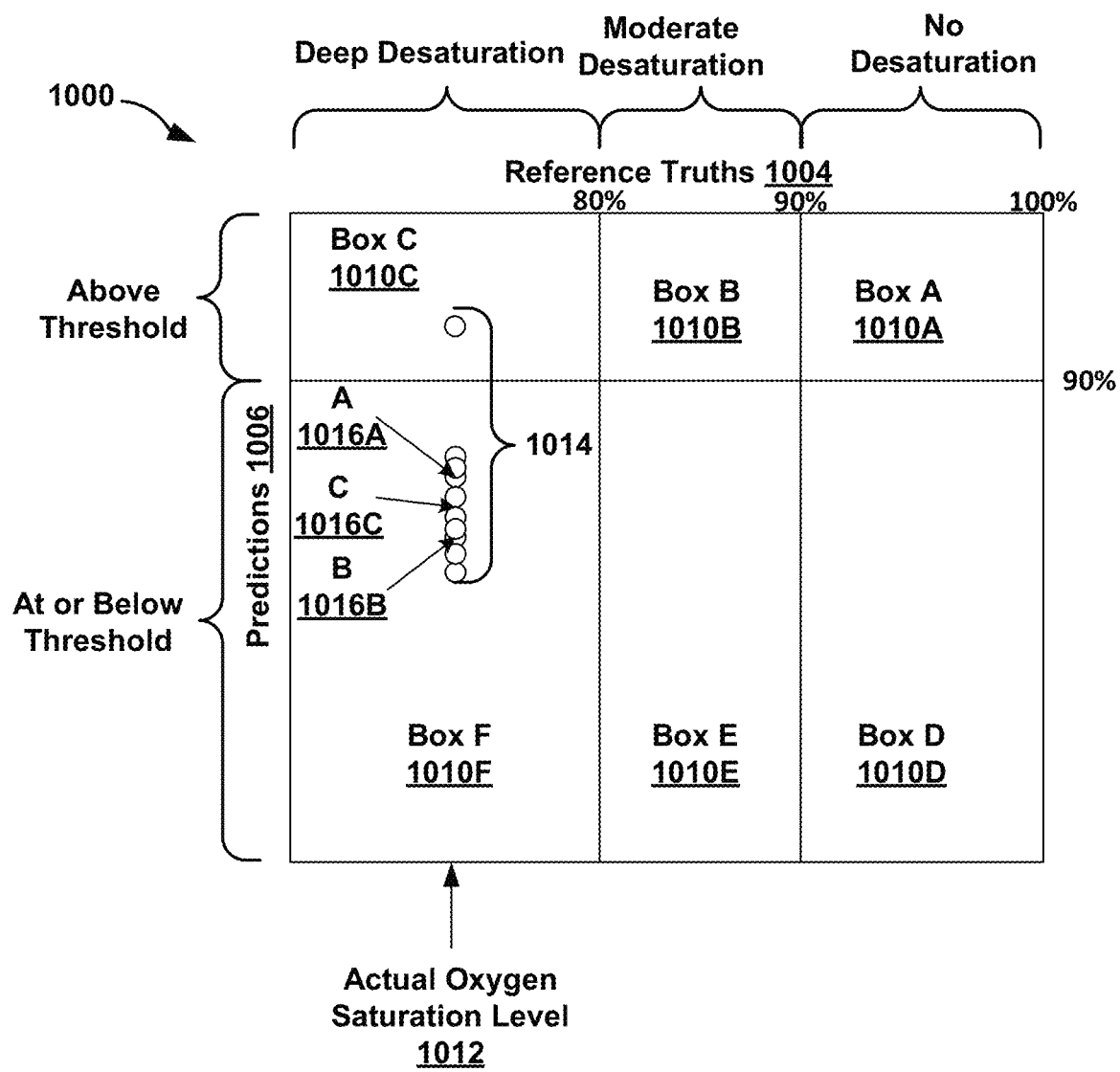
FIG. 10 illustrates an example spread of predictions made using a plurality of oxygen saturation prediction models.

FIG. 10 illustrates an example spread of predictions made using a plurality of oxygen saturation prediction models. Similar to graph 500 of FIG. 5, graph 1000 is a graph of reference truths 1004 of actual oxygen saturation levels of one or more patients at the end of a predetermined time period versus predictions 1006 made by processing circuitry 110 of the oxygen saturation levels of the one or more patients at the end of the predetermined time period. Graph 1000 includes box A 1010A, box B 1010B, box C 1010C, box D 1010D, box E 1010E, and box F 1010F. Box A 1010A, box B 1010B, and box C 1010C are boxes where processing circuitry 110 of oxygen saturation monitoring device 100 predicts that the oxygen saturation levels of one or more patients will increase above the desaturation threshold by the end of a predefined time period, and therefore refrains from outputting notifications indicative of oxygen desaturation events. Box D 1010D, box E 1010E, and box F 1010F are boxes where processing circuitry 110 predicts that the oxygen saturation level of one or more patients will not increase above the desaturation threshold by the end of a predefined time period. As such, processing circuitry 110 may output notifications at the prediction point that are indicative of patients experiencing oxygen desaturation events.

In particular, box C 1010C is a box where the actual oxygen saturation level of patient 101 decreases below a deep desaturation threshold by the end of a predefined time period and where processing circuitry 110 incorrectly predicts that the actual oxygen saturation level of patient 101 will be above the saturation threshold by the end of the predefined period. Aspects of the present disclosure include techniques for minimizing the number of predicted oxygen saturation levels that end up in box C 1010C in examples in which processing circuitry 110 executes oxygen saturation prediction model 124 to generate a plurality of predicted oxygen saturation levels.

As shown in FIG. 10, the actual oxygen saturation level 1012 at the end of a predetermined time period for patient 101 is below a deep desaturation threshold. As such, processing circuitry 110 may correctly predict the oxygen saturation level for patient 101 at the end of the predefined time period if processing circuitry 110 determines a predicted oxygen saturation level for patient 101 that is in box F 1010F.

Meanwhile, processing circuitry 110 may generate a plurality of predicted oxygen saturation levels 1014 at the end of the predetermined time period for patient 101. As can be seen, while most of the plurality of predicted oxygen saturation levels 1014 are in box F 1010F, one of the plurality of predicted oxygen saturation levels 1014 is in box C 1010C. If processing circuitry 110 had only determined a single predicted oxygen saturation level in box C 1010C, the predicted oxygen saturation level may have led oxygen saturation monitoring device 100 to incorrectly refrain from outputting a notification indicative of an oxygen desaturation event at a particular time (though processing circuitry 110 may have eventually provided a notification as discussed above).

In some examples, processing circuitry 110 may average the plurality of predicted oxygen saturation levels 1014 to determine an average predicted oxygen saturation level that is at point A 1016A in graph 1000. Although point A 1016A is in box F 1010F, the average of the plurality of predicted oxygen saturation levels 1014 is still skewed by the predicted oxygen saturation level in box C 1010C. As such, processing circuitry 110 may apply a skew to the plurality of predicted oxygen saturation levels 1014 to determine an average predicted oxygen saturation level.

For example, processing circuitry 110 may select the predicted oxygen saturation levels that are in the bottom $50^{th}$ percentile of the plurality of predicted oxygen saturation levels 1014 and may average the selected predicted oxygen saturation levels to determine an average predicted oxygen saturation level that is at point B 1016B in graph 1000. In some examples, processing circuitry 110 may bias the average predicted oxygen saturation level that is at point B 1016B in graph 1000 by adding a bias value to the average predicted oxygen saturation level to result in a biased and skewed average predicted oxygen saturation level that is at point C 1016C in graph 1000.

Figure 11:
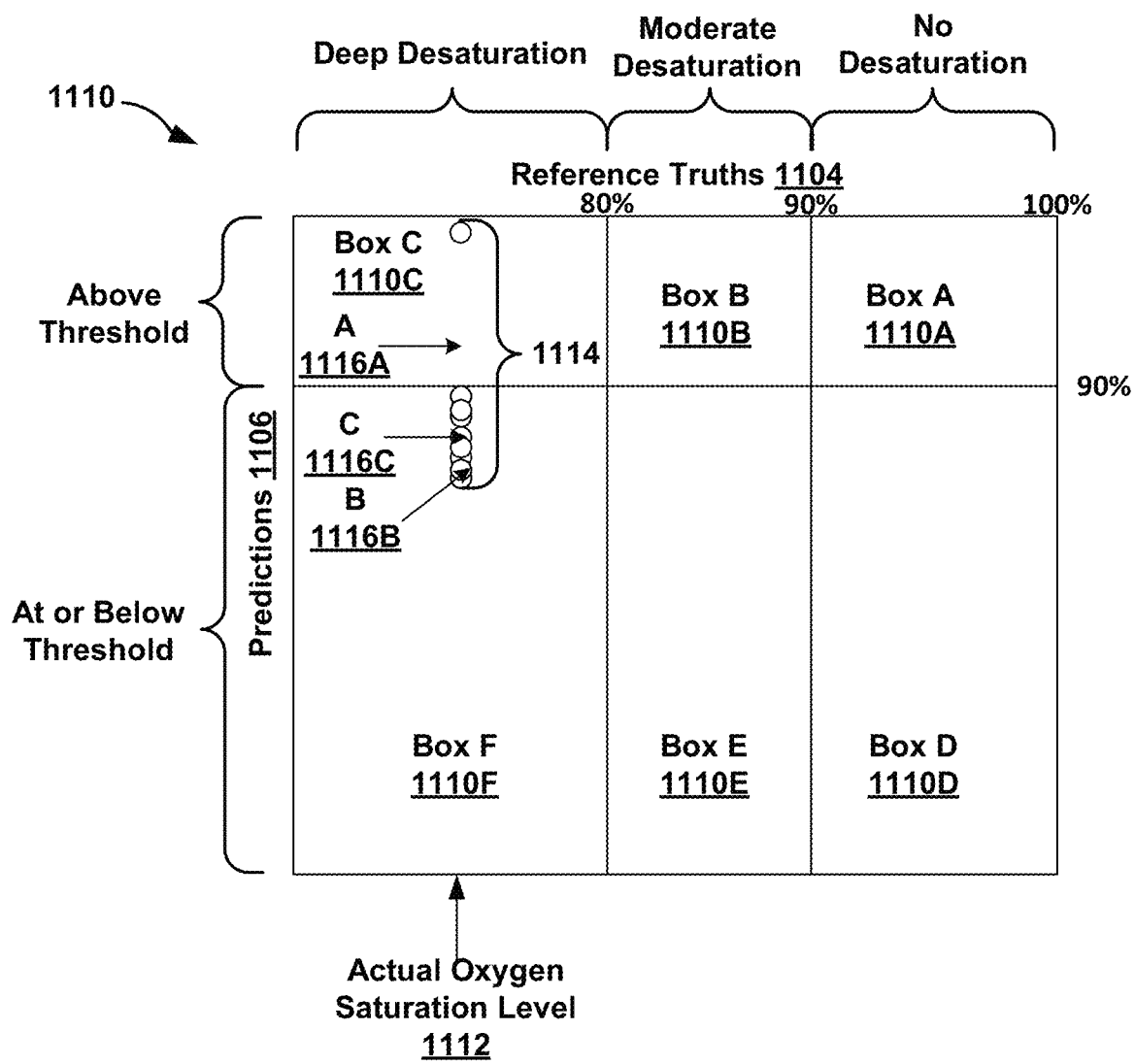
FIG. 11 illustrates another example spread of predictions made using a plurality of oxygen saturation prediction models.

FIG. 11 illustrates an example spread of predictions made using a plurality of oxygen saturation prediction models. Similar to graph 500 of FIG. 5, graph 1100 is a graph of reference truths 1104 of actual oxygen saturation levels of one or more patients at the end of a predetermined time period versus predictions 1106 made by processing circuitry 110 of the oxygen saturation levels of the one or more patients at the end of the predetermined time period. Graph 1100 includes box A 1110A, box B 1110B, box C 1110C, box D 1110D, box E 1110E, and box F 1110F. Box A 1110A, box B 1110B, and box C 1110C are boxes where processing circuitry 110 of oxygen saturation monitoring device 100 predicts that the oxygen saturation levels of one or more patients will increase above the desaturation threshold by the end of a predefined time period, and therefore refrains from outputting notifications indicative of oxygen desaturation events. Box D 1110D, box E 1110E, and box F 1110F are boxes where processing circuitry 110 predicts that the oxygen saturation level of one or more patients will not increase above the desaturation threshold by the end of a predefined time period. As such, processing circuitry 110 may output notifications at the prediction point that are indicative of patients experiencing oxygen desaturation events.

In particular, box C 1110C is a box where the actual oxygen saturation level of patient 101 decreases below a deep desaturation threshold by the end of a predefined time period and where processing circuitry 110 incorrectly predicts that the actual oxygen saturation level of patient 101 will be above the saturation threshold by the end of the predefined period. If processing circuitry 110 executes oxygen saturation prediction model 124 to generate a plurality of predicted oxygen saturation levels, then processing circuitry 110 may implement one or more techniques described herein to help minimize the number of predicted oxygen saturation levels that end up in box C 1110C.

As shown in FIG. 11, the actual oxygen saturation level 1112 at the end of a predetermined time period for patient 101 is below a deep desaturation threshold. As such, processing circuitry 110 may correctly predict the oxygen saturation level for patient 101 at the end of the predetermined time period if processing circuitry 110 determines a predicted oxygen saturation level for patient 101 that is in box F 1110F.

Meanwhile, processing circuitry 110 may generate a plurality of predicted oxygen saturation levels 1114 at the end of the predefined time period for patient 101. As can be seen, while most of the plurality of predicted oxygen saturation levels 1114 are in box F 1010F, one of the plurality of predicted oxygen saturation levels 1114 is in box C 1110C. If processing circuitry 110 had only determined a single predicted oxygen saturation level in box C 1110C, then the predicted oxygen saturation level may have led oxygen saturation monitoring device 100 to incorrectly refrain from outputting a notification indicative of an oxygen desaturation event at a particular time.

In some examples, processing circuitry 110 may average the plurality of predicted oxygen saturation levels 1114 to determine an average predicted oxygen saturation level that is at point A 1116A in graph 1100. As can be seen, the average of the plurality of predicted oxygen saturation levels 1010 is skewed by the large distance between the predicted oxygen saturation level in box C 1110C and the rest of the plurality of predicted oxygen saturation levels 1114 so that the average predicted oxygen saturation level that is at point A 1116A in graph 1100 is in box C 1110C.

As such, processing circuitry 110 may apply a skew to the plurality of predicted oxygen saturation levels 1110 to determine an average predicted oxygen saturation level that is not in box C 1110C. For example, processing circuitry 110 may select the predicted oxygen saturation levels that are in the bottom $50^{th}$ percentile of the plurality of predicted oxygen saturation levels 1110 and may average the selected predicted oxygen saturation levels to determine an average predicted oxygen saturation level that is at point B 1116B in graph 1100. In some examples, processing circuitry 110 may bias the average predicted oxygen saturation level that is at point B 1116B in graph 1110 by adding a predetermined bias value to the average predicted oxygen saturation level to result in a biased and skewed average predicted oxygen saturation level that is at point C 1116C in graph 1110.

Figure 12:
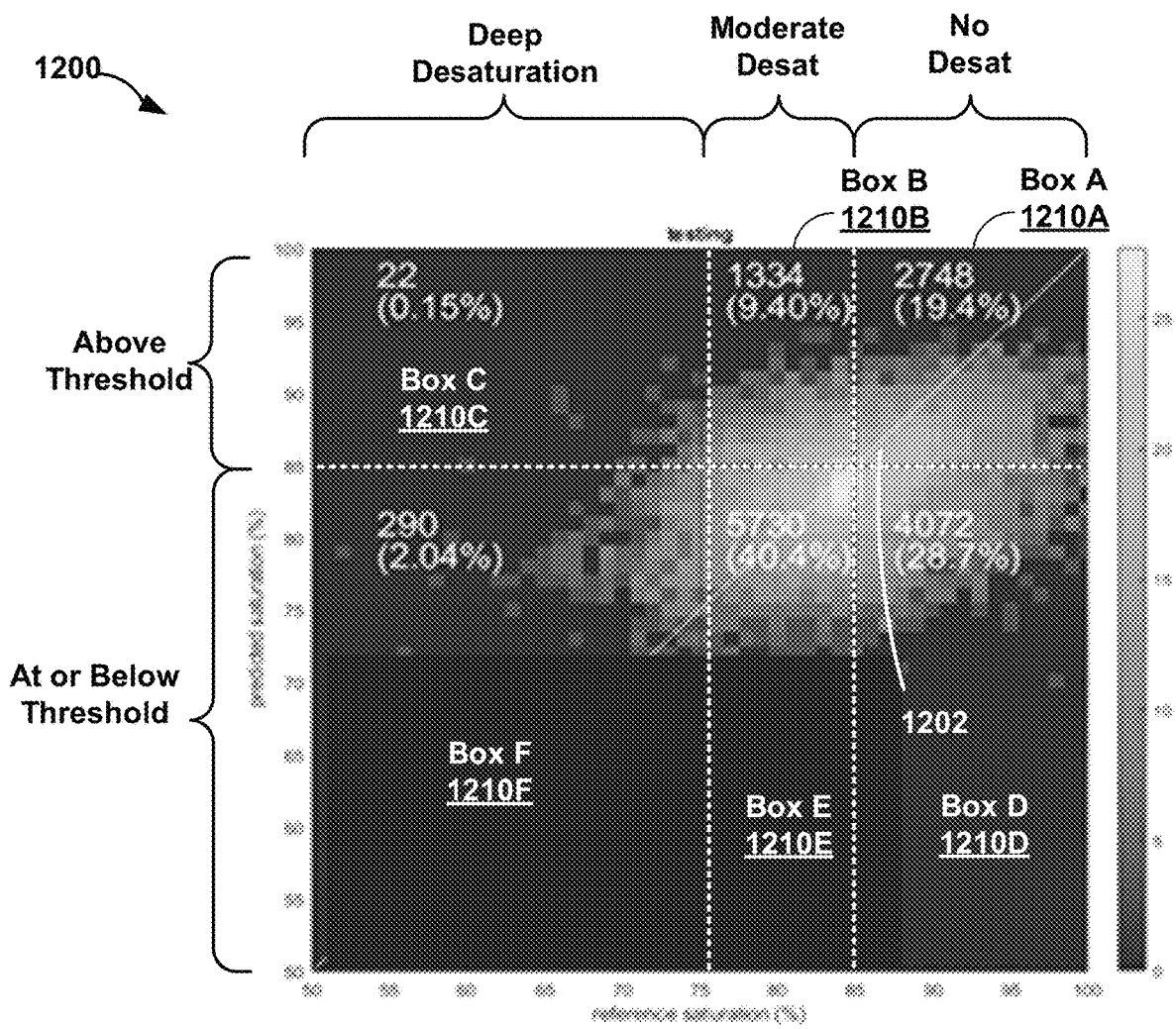
FIG. 12 illustrates an example spread of prediction points versus the reference truth of predictions made using a single oxygen saturation prediction model over a sample set of data.

FIG. 12 illustrates an example spread of prediction points versus the reference truth of predictions made using a single oxygen saturation prediction model over a sample set of data. As shown in FIG. 12, graph 1200 is a density plot of prediction points collected from patients. Similar to graph 500 of FIG. 5, graph 1200 includes box A 1210A, box B 1210B, box C 1210C, box D 1210D, box E 1210E, and box F 1210F.

The following table lists the number of prediction points 1202 in each of box A 1210A, box B 1210B, box C 1210C, box D 1210D, box E 1210E, and box F 1210F in graph 600:

| Box | Number of Prediction Points |
|---|---|
| A | 2,748 |
| B | 1,334 |
| C | 22 |
| D | 4,072 |
| E | 5,730 |
| F | 290 |
| Total | 8,521 |

Figure 13:
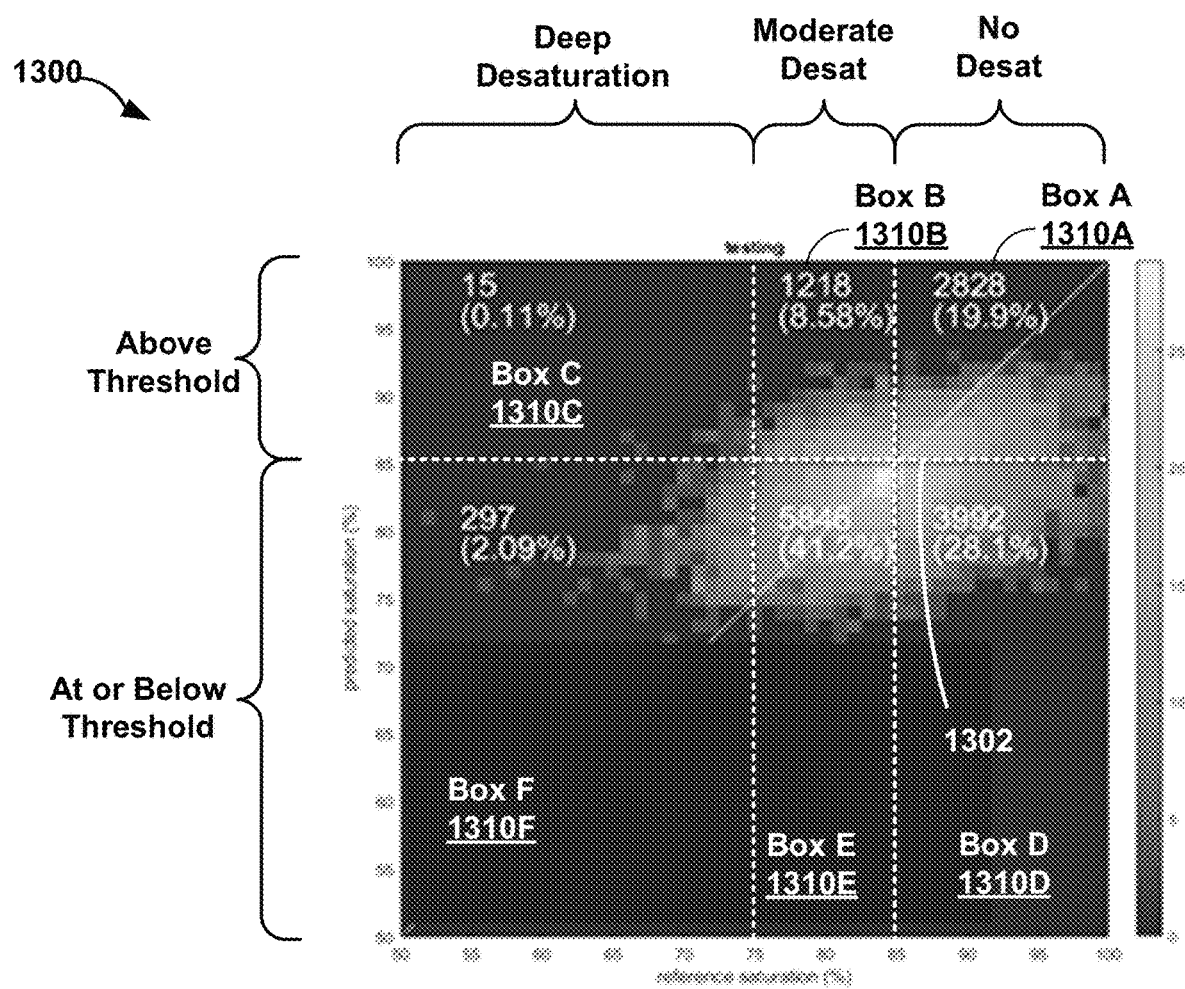
FIG. 13 illustrates an example spread of prediction points versus the reference truth of predictions made using a plurality of oxygen saturation prediction models over the same sample set of data as in FIG. 12.

FIG. 13 illustrates an example spread of prediction points versus the reference truth of predictions made using a plurality of oxygen saturation prediction models over the same sample set of data as in FIG. 12, e.g., using the techniques described with reference to FIGS. 10 and 11. As shown in FIG. 13, graph 1300 is a density plot of prediction points collected from patients, where each prediction point is determined using predictions from twelve oxygen saturation prediction models. Similar to graph 500 of FIG. 5, graph 1300 includes box A 1310A, box B 1310B, box C 1310C, box D 1310D, box E 1310E, and box F 1310F.

The following table lists the number of prediction points 1302 in each of box A 1310A, box B 1310B, box C 1310C, box D 1310D, box E 1310E, and box F 1310F in graph 600:

| Box | Number of Prediction Points |
|---|---|
| A | 2,848 |
| B | 1,218 |
| C | 15 |
| D | 3,992 |
| E | 5,846 |
| F | 297 |
| Total | 8,521 |

As can be seen, compared with the prediction points 1202 in FIG. 12, the number of prediction points 1302 in box C 1310C has decreased from 22 to 15, while the number of prediction points 1392 in box A 1310A has increased from 2,748 to 2,828. As such, predicting saturation events and deep desaturation events can be improved by using a plurality of predictions made using a plurality of oxygen saturation prediction models versus using a single oxygen saturation prediction model.

Figure 14:
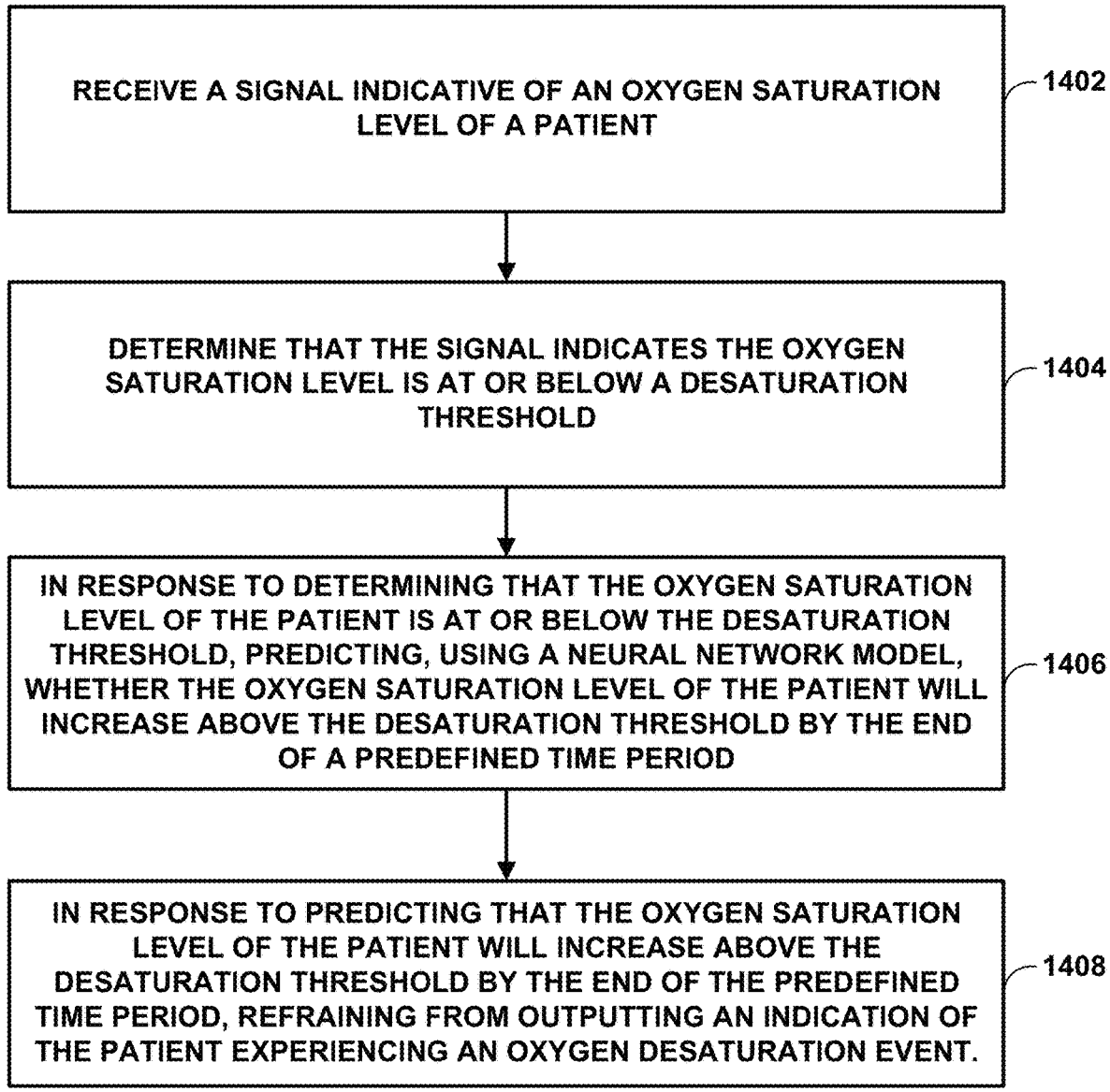
FIG. 14 is a flow diagram illustrating an example method for predicting the oxygen saturation level of a patient at the end of a predefined time period using the example oxygen saturation prediction model of FIG. 1.

FIG. 14 is a flow diagram illustrating an example method for predicting the oxygen saturation level of a patient at the end of a predefined time period using the example oxygen saturation prediction model 124 of FIG. 1. Although FIG. 14 is described with respect to processing circuitry 110 of oxygen saturation monitoring device 100 (FIG. 1), in other examples, different processing circuitry, alone or in combination with processing circuitry 110, may perform any part of the technique of FIG. 14.

The technique illustrated in FIG. 14 includes receiving, by processing circuitry 110, a signal indicative of an oxygen saturation level of a patient 101 (1402). For example, processing circuitry 110 may receive a signal from oxygen saturation sensing circuitry 140 (FIG. 1) or control circuitry 122 (FIG. 1), or a different sensor. The technique further includes determining, by the processing circuitry 110, that the signal indicates the oxygen saturation level is at or below a desaturation threshold (1404). In response to determining the oxygen saturation level of the patient 101 is at or below the desaturation threshold, processing circuitry 110 predicts, using an oxygen saturation prediction model 124, whether the oxygen saturation level of the patient 101 will increase above the desaturation threshold by the end of a predefined time period (1406). In response to predicting that the oxygen saturation level of the patient 101 will increase above the desaturation threshold by the end of the predefined time period, processing circuitry 110 refrains from outputting an indication of the patient 101 experiencing an oxygen desaturation event (1408).

In some examples, the technique further includes, in response to predicting that the oxygen saturation level of the patient 101 will increase above the desaturation threshold by the end of the predefined time period, determining, by the processing circuitry 110 and prior to the end of the predefined time period, whether the oxygen saturation level of the patient 101 has decreased below a deep desaturation threshold and in response to determining that the oxygen saturation level of the patient 101 has decreased below the deep desaturation threshold, outputting an indication of the patient 101 experiencing a deep oxygen desaturation event.

In some examples, the techniques further include in response to predicting that the oxygen saturation level of the patient 101 will increase above the desaturation threshold within the predefined time period, determining, by the processing circuitry 110 and prior to the predefined time period ending, whether the oxygen saturation level of the patient 101 is continuing to decrease and in response to determining that the oxygen saturation level of the patient 101 is continuing to decrease, outputting the indication of the patient 101 experiencing the oxygen desaturation event.

In some examples, to predict, using the oxygen saturation prediction model 124, whether the oxygen saturation level of the patient 101 will increase above the desaturation threshold within a predefined time period, the techniques may further include inputting one or more of: a history of oxygen saturation levels of the patient 101 over a time period immediately prior to the oxygen saturation level of the patient 101 being at or below the desaturation threshold, a history of blood pressure values of the patient 101 over the time period, or one or more metrics derived from photoplethysmographic (PPG) signals of the patient 101 over the time period into the oxygen saturation prediction model 124 to predict whether the oxygen saturation level of the patient 101 will increase above the desaturation threshold within the predefined time period.

In some examples, the one or more metrics derived from the PPG signals of the patient 101 comprises one or more of: PPG pulse skews, PPG pulse amplitudes, normalized amplitudes of PPG pulses, PPG pulse maximum slope, a location of the PPG pulse maximum slope, PPG pulse maximum curvature, or a location of the PPG pulse maximum curvature.

In some examples, oxygen saturation prediction model comprises a neural network algorithm trained via machine learning over training data that includes one or more of: sets of blood oxygen level of a population of patients, sets of blood pressure values of the population of patients, or metrics derived from sets of PPG signals of the population of patients.

In some examples, the techniques further include retraining the neural network algorithm to minimize incorrect predictions made using the oxygen saturation prediction model of oxygen saturation levels of the patient 101 that miss deep oxygen desaturation events experienced by the patient 101.

In some examples, the techniques further include determining, by the processing circuitry 110, offsets between oxygen saturation levels predicted using the oxygen saturation prediction model 124 and actual oxygen saturation levels of the patient 101 and calibrating, by the processing circuitry 110, the oxygen saturation prediction model 124 based at least in part on the determined offsets.

In some examples, the techniques further include determining, by the processing circuitry 110 and at the end of the predefined time period, whether the oxygen saturation level of the patient 101 is above the desaturation threshold and in response to determining that the oxygen saturation level of the patient 101 is not above the desaturation threshold, outputting, by the processing circuitry 110, the indication of the patient 101 experiencing the oxygen desaturation event.

In some examples, predicting, using the oxygen saturation prediction model 124, whether the oxygen saturation level of the patient 101 will increase above the desaturation threshold by the end of a predefined time period further includes determining, by the processing circuitry 110 and using a plurality of oxygen saturation prediction models, a plurality of predictions of whether the oxygen saturation level of the patient 101 will increase above the desaturation threshold by the end of a predefined time period and predicting, by the processing circuitry 110 and based at least in part on the plurality of predictions, whether the oxygen saturation level of the patient 101 will increase above the desaturation threshold by the end of a predefined time period.

In some examples, the plurality of oxygen saturation prediction models comprise a plurality of neural network algorithms trained via machine learning.

In some examples, to predict, based at least in part on the plurality of predictions, whether the oxygen saturation level of the patient 101 will increase above the desaturation threshold by the end of a predefined time period, the techniques may further include determining, by the processing circuitry 110, an average predicted oxygen saturation level by the end of the predefined time period from two or more of the plurality of predictions and predicting, by the processing circuitry 110 and based at least in part on the average predicted oxygen saturation level by the end of the predefined time period, whether the oxygen saturation level of the patient 101 will increase above the desaturation threshold by the end of a predefined time period.

In some examples, to determine the average predicted oxygen saturation level by the end of the predefined time period from the two or more of the plurality of predictions, the techniques further include determining, by the processing circuitry 110, a weighted average predicted oxygen saturation level by the end of the predefined time period from the two or more of the plurality of predictions. In some examples, to predict whether the oxygen saturation level of the patient will increase above the desaturation threshold by the end of a predefined time period, the techniques further include predicting, by the processing circuitry 110 and based at least in part on the weighted average predicted oxygen saturation level by the end of the predefined time period, whether the oxygen saturation level of the patient 101 will increase above the desaturation threshold by the end of a predefined time period.

In some examples, to determine the average predicted oxygen saturation level by the end of the predefined time period from the two or more of the plurality of predictions, the techniques further include adding, by the processing circuitry 110, a bias to the average predicted oxygen saturation level to determine a biased average predicted oxygen saturation level. In some examples, to predict whether the oxygen saturation level of the patient will increase above the desaturation threshold by the end of a predefined time period, the techniques further include predicting, by the processing circuitry 110 and based at least in part on the biased average predicted oxygen saturation level by the end of the predefined time period, whether the oxygen saturation level of the patient 101 will increase above the desaturation threshold by the end of a predefined time period.

In some examples, the techniques further include selecting, by the processing circuitry 110, the two or more of the plurality of predictions based at least in part on the two or more of the plurality of predictions being within a specified percentile of the plurality of predictions of whether the oxygen saturation level of the patient 101 will increase above the desaturation threshold by the end of a predefined time period.

In some examples, the techniques further include determining, by the processing circuitry 110, one or more outlier predictions from the plurality of predictions and refraining, by the processing circuitry 110, from including the one or more outlier predictions in the two or more of the plurality of predictions.

The techniques described in this disclosure, including those attributed to device 100, processing circuitry 110, control circuitry 122, sensing circuitries 140, 142, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

Example 1: A method that includes receiving, by processing circuitry, a signal indicative of an oxygen saturation level of a patient; determining, by the processing circuitry, that the signal indicates the oxygen saturation level is at or below a desaturation threshold; in response to determining the oxygen saturation level of the patient is at or below the desaturation threshold, predicting, by the processing circuitry and using an oxygen saturation prediction model, whether the oxygen saturation level of the patient will increase above the desaturation threshold by the end of a predefined time period; and in response to predicting that the oxygen saturation level of the patient will increase above the desaturation threshold by the end of the predefined time period, refraining from outputting an indication of the patient experiencing an oxygen desaturation event.

Example 2: The method of example 1, further that includes in response to predicting that the oxygen saturation level of the patient will increase above the desaturation threshold by the end of the predefined time period, determining, by the processing circuitry and prior to the end of the predefined time period, whether the oxygen saturation level of the patient has decreased below a deep desaturation threshold; and in response to determining that the oxygen saturation level of the patient has decreased below the deep desaturation threshold, outputting an indication of the patient experiencing a deep oxygen desaturation event.

Example 3: The method of any of examples 1 and 2, further that includes in response to predicting that the oxygen saturation level of the patient will increase above the desaturation threshold within the predefined time period, determining, by the processing circuitry and prior to the predefined time period ending, whether the oxygen saturation level of the patient is continuing to decrease; and in response to determining that the oxygen saturation level of the patient is continuing to decrease, outputting the indication of the patient experiencing the oxygen desaturation event.

Example 4: The method of any of examples 1-3, wherein predicting, using the oxygen saturation prediction model, whether the oxygen saturation level of the patient will increase above the desaturation threshold within the predefined time period comprises: inputting one or more of: a history of oxygen saturation levels of the patient over a time period immediately prior to the oxygen saturation level of the patient being at or below the desaturation threshold, a history of blood pressure values of the patient over the time period, or one or more metrics derived from photoplethysmographic (PPG) signals of the patient over the time period into the oxygen saturation prediction model to predict whether the oxygen saturation level of the patient will increase above the desaturation threshold within the predefined time period.

Example 5: The method of example 4, wherein the one or more metrics derived from the PPG signals of the patient comprises one or more of: PPG pulse skews, PPG pulse amplitudes, normalized amplitudes of PPG pulses, PPG pulse maximum slope, a location of the PPG pulse maximum slope, PPG pulse maximum curvature, or a location of the PPG pulse maximum curvature.

Example 6: The method of any of examples 1-5, wherein the oxygen saturation prediction model comprises a neural network algorithm trained via machine learning over training data that includes one or more of: sets of blood oxygen level of a population of patients, sets of blood pressure values of the population of patients, or metrics derived from sets of PPG signals of the population of patients.

Example 7: The method of example 6, further that includes retraining the neural network algorithm to minimize incorrect predictions made using the oxygen saturation prediction model of oxygen saturation levels of the patient that miss deep oxygen desaturation events experienced by the patient.

Example 8: The method of any of examples 1-7, further that includes determining, by the processing circuitry, offsets between oxygen saturation levels predicted using the oxygen saturation prediction model and actual oxygen saturation levels of the patient; and calibrating, by the processing circuitry, the oxygen saturation prediction model based at least in part on the determined offsets.

Example 9: The method of any of examples 1-8, further that includes determining, by the processing circuitry and at the end of the predefined time period, whether the oxygen saturation level of the patient is above the desaturation threshold; and in response to determining that the oxygen saturation level of the patient is not above the desaturation threshold, outputting, by the processing circuitry, the indication of the patient experiencing the oxygen desaturation event.

Example 10: The method of any of examples 1-9, wherein predicting, using the oxygen saturation prediction model, whether the oxygen saturation level of the patient will increase above the desaturation threshold by the end of the predefined time period further comprises: determining, by the processing circuitry and using a plurality of oxygen saturation prediction models, a plurality of predictions of whether the oxygen saturation level of the patient will increase above the desaturation threshold by the end of the predefined time period; and predicting, by the processing circuitry and based at least in part on the plurality of predictions, whether the oxygen saturation level of the patient will increase above the desaturation threshold by the end of the predefined time period.

Example 11: The method of example 10, wherein the plurality of oxygen saturation prediction models comprise a plurality of neural network algorithms trained via machine learning.

Example 12: The method of example 10, wherein predicting, based at least in part on the plurality of predictions, whether the oxygen saturation level of the patient will increase above the desaturation threshold by the end of the predefined time period further comprises: determining, by the processing circuitry, an average predicted oxygen saturation level by the end of the predefined time period from two or more of the plurality of predictions; and predicting, by the processing circuitry and based at least in part on the average predicted oxygen saturation level by the end of the predefined time period, whether the oxygen saturation level of the patient will increase above the desaturation threshold by the end of the predefined time period.

Example 13: The method of example 12, wherein determining the average predicted oxygen saturation level by the end of the predefined time period from the two or more of the plurality of predictions further comprises: determining, by the processing circuitry, a weighted average predicted oxygen saturation level by the end of the predefined time period from the two or more of the plurality of predictions, wherein predicting whether the oxygen saturation level of the patient will increase above the desaturation threshold by the end of the predefined time period further comprises predicting, by the processing circuitry and based at least in part on the weighted average predicted oxygen saturation level, whether the oxygen saturation level of the patient will increase above the desaturation threshold by the end of the predefined time period.

Example 14: The method of example 12, wherein determining the average predicted oxygen saturation level by the end of the predefined time period from the two or more of the plurality of predictions further comprises: adding, by the processing circuitry, a bias to the average predicted oxygen saturation level to determine a biased average predicted oxygen saturation level, wherein predicting whether the oxygen saturation level of the patient will increase above the desaturation threshold by the end of the predefined time period further comprises predicting, by the processing circuitry and based at least in part on the biased average predicted oxygen saturation level, whether the oxygen saturation level of the patient will increase above the desaturation threshold by the end of the predefined time period.

Example 15: The method of example 12, further that includes selecting, by the processing circuitry, the two or more of the plurality of predictions based at least in part on the two or more of the plurality of predictions being within a specified percentile of the plurality of predictions.

Example 16: The method of example 12, further that includes determining, by the processing circuitry, one or more outlier predictions from the plurality of predictions; and refraining, by the processing circuitry, from including the one or more outlier predictions in the two or more of the plurality of predictions.

Example 17: A system that includes an oxygen saturation sensing device configured to sense an oxygen saturation level of a patient; and processing circuitry configured to: receive a signal indicative of the oxygen saturation level of the patient; determining, by the processing circuitry, that the signal indicates the oxygen saturation level is at or below a desaturation threshold; in response to determining the oxygen saturation level of the patient is at or below the desaturation threshold, predict, using an oxygen saturation prediction model, whether the oxygen saturation level of the patient will increase above the desaturation threshold by the end of a predefined time period; and in response to predicting that the oxygen saturation level of the patient will increase above the desaturation threshold by the end of the predefined time period, refrain from outputting an indication of the patient experiencing an oxygen desaturation event.

Example 18: The system of example 17, wherein the processing circuitry is further configured to: in response to predicting that the oxygen saturation level of the patient will increase above the desaturation threshold by the end of the predefined time period, determine, prior to the end of the predefined time period, whether the oxygen saturation level of the patient has decreased below a deep desaturation threshold; and in response to determining that the oxygen saturation level of the patient has decreased below the deep desaturation threshold, output an indication of the patient experiencing a deep oxygen desaturation event.

Example 19: The system of any of examples 17 and 18, wherein the processing circuitry is further configured to: in response to predicting that the oxygen saturation level of the patient will increase above the desaturation threshold within the predefined time period, determine, prior to the predefined time period ending, whether the oxygen saturation level of the patient is continuing to decrease; and in response to determining that the oxygen saturation level of the patient is continuing to decrease, outputting the indication of the patient experiencing the oxygen desaturation event.

Example 20: The system of any of examples 17-19, wherein to predict, using the oxygen saturation prediction model, whether the oxygen saturation level of the patient will increase above the desaturation threshold within the predefined time period, the processing circuitry is further configured to: inputting one or more of: a history of oxygen saturation levels of the patient over a time period immediately prior to the oxygen saturation level of the patient being at or below the desaturation threshold, a history of blood pressure values of the patient over the time period, or one or more metrics derived from photoplethysmographic (PPG) signals of the patient over the time period into the oxygen saturation prediction model to predict whether the oxygen saturation level of the patient will increase above the desaturation threshold within the predefined time period.

Example 21: The system of example 20, wherein the one or more metrics derived from the PPG signals of the patient comprises one or more of: PPG pulse skews, PPG pulse amplitudes, normalized amplitudes of PPG pulses, PPG pulse maximum slope, a location of the PPG pulse maximum slope, PPG pulse maximum curvature, or a location of the PPG pulse maximum curvature.

Example 22: The system of any of examples 17-21, wherein the oxygen saturation prediction model comprises a neural network algorithm trained via machine learning over training data that includes one or more of: sets of blood oxygen level of a population of patients, sets of blood pressure values of the population of patients, or metrics derived from sets of PPG signals of the population of patients.

Example 23: The system of example 22, wherein the processing circuitry is further configured to: retrain the neural network algorithm to minimize incorrect predictions made using the oxygen saturation prediction model of oxygen saturation levels of the patient that miss deep oxygen desaturation events experienced by the patient.

Example 24: The system of example 17, wherein the processing circuitry is further configured to: determine offsets between oxygen saturation levels predicted using the oxygen saturation prediction model and actual oxygen saturation levels of the patient; and calibrate the oxygen saturation prediction model based at least in part on the determined offsets.

Example 25: The system of any of examples 17-24, wherein the processing circuitry is further configured to: determine, at the end of the predefined time period, whether the oxygen saturation level of the patient is above the desaturation threshold; and in response to determining that the oxygen saturation level of the patient is not above the desaturation threshold, output the indication of the patient experiencing the oxygen desaturation event.

Example 26: The system of example 17, wherein to predict, using the oxygen saturation prediction model, whether the oxygen saturation level of the patient will increase above the desaturation threshold by the end of the predefined time period, the processing circuitry is further configured to: determine, using a plurality of oxygen saturation prediction models, a plurality of predictions of whether the oxygen saturation level of the patient will increase above the desaturation threshold by the end of the predefined time period; and predict, based at least in part on the plurality of predictions, whether the oxygen saturation level of the patient will increase above the desaturation threshold by the end of the predefined time period.

Example 27: The system of example 26, wherein the plurality of oxygen saturation prediction models comprise a plurality of neural network algorithms trained via machine learning.

Example 28: The system of example 26, wherein to predict, based at least in part on the plurality of predictions, whether the oxygen saturation level of the patient will increase above the desaturation threshold by the end of the predefined time period, the processing circuitry is further configured to: determine an average predicted oxygen saturation level by the end of the predefined time period from two or more of the plurality of predictions; and predict, based at least in part on the average predicted oxygen saturation level by the end of the predefined time period, whether the oxygen saturation level of the patient will increase above the desaturation threshold by the end of the predefined time period.

Example 29: The system of example 28, wherein to determine the average predicted oxygen saturation level by the end of the predefined time period from the two or more of the plurality of predictions, the processing circuitry is further configured to: determine a weighted average predicted oxygen saturation level by the end of the predefined time period from the two or more of the plurality of predictions, wherein to predict whether the oxygen saturation level of the patient will increase above the desaturation threshold by the end of the predefined time period, the processing circuitry is further configured to predict, based at least in part on the weighted average predicted oxygen saturation level, whether the oxygen saturation level of the patient will increase above the desaturation threshold by the end of the predefined time period.

Example 30: The system of example 28, wherein to determine the average predicted oxygen saturation level by the end of the predefined time period from the two or more of the plurality of predictions, the processing circuitry is further configured to: add a bias to the average predicted oxygen saturation level to determine a biased average predicted oxygen saturation level; and wherein to predict whether the oxygen saturation level of the patient will increase above the desaturation threshold by the end of the predefined time period, the processing circuitry is further configured to predict, based at least in part on the biased average predicted oxygen saturation level, whether the oxygen saturation level of the patient will increase above the desaturation threshold by the end of the predefined time period.

Example 31: The system of example 28, wherein the processing circuitry is further configured to: select the two or more of the plurality of predictions based at least in part on the two or more of the plurality of predictions being within a specified percentile of the plurality of predictions.

Example 32: The system of example 28, wherein the processing circuitry is further configured to: determine one or more outlier predictions from the plurality of predictions; and refrain from including the one or more outlier predictions in the two or more of the plurality of predictions.

Example 33: A non-transitory computer readable storable medium comprising instructions that, when executed, cause processing circuitry to: receive a signal indicative of an oxygen saturation level of a patient; determining, by the processing circuitry, that the signal indicates the oxygen saturation level is at or below a desaturation threshold; in response to determining the oxygen saturation level of the patient is at or below the desaturation threshold, predict, using an oxygen saturation prediction model, whether the oxygen saturation level of the patient will increase above the desaturation threshold by the end of a predefined time period; and in response to predicting that the oxygen saturation level of the patient will increase above the desaturation threshold by the end of the predefined time period, refrain from outputting an indication of the patient experiencing an oxygen desaturation event.

Various examples of the disclosure have been described. Any combination of the described systems, operations, or functions is contemplated. These and other examples are within the scope of the following claims.

What is claimed is:

1. A method comprising:
   receiving, by processing circuitry, a signal indicative of an oxygen saturation level of a patient;
   determining, by the processing circuitry, that the signal indicates the oxygen saturation level is at or below a desaturation threshold;
   in response to determining the oxygen saturation level of the patient is at or below the desaturation threshold, predicting, by the processing circuitry and using an oxygen saturation prediction model, whether the oxygen saturation level of the patient will increase above the desaturation threshold by the end of a predefined time period; and
   in response to predicting that the oxygen saturation level of the patient will increase above the desaturation threshold by the end of the predefined time period, refraining from outputting an indication of the patient experiencing an oxygen desaturation event.

2. The method of claim 1, further comprising:
   in response to predicting that the oxygen saturation level of the patient will increase above the desaturation threshold by the end of the predefined time period, determining, by the processing circuitry and prior to the end of the predefined time period, whether the oxygen saturation level of the patient has decreased below a deep desaturation threshold; and
   in response to determining that the oxygen saturation level of the patient has decreased below the deep desaturation threshold, outputting an indication of the patient experiencing a deep oxygen desaturation event.

3. The method of claim 1, further comprising:
   in response to predicting that the oxygen saturation level of the patient will increase above the desaturation threshold within the predefined time period, determining, by the processing circuitry and prior to the predefined time period ending, whether the oxygen saturation level of the patient is continuing to decrease; and in response to determining that the oxygen saturation level of the patient is continuing to decrease, outputting the indication of the patient experiencing the oxygen desaturation event.

4. The method of claim 1, wherein predicting, using the oxygen saturation prediction model, whether the oxygen saturation level of the patient will increase above the desaturation threshold within the predefined time period comprises:

inputting one or more of: a history of oxygen saturation levels of the patient over a time period immediately prior to the oxygen saturation level of the patient being at or below the desaturation threshold, a history of blood pressure values of the patient over the time period, or one or more metrics derived from photoplethysmographic (PPG) signals of the patient over the time period into the oxygen saturation prediction model to predict whether the oxygen saturation level of the patient will increase above the desaturation threshold within the predefined time period.

5. The method of claim 4, wherein the one or more metrics derived from the PPG signals of the patient comprises one or more of: PPG pulse skews, PPG pulse amplitudes, normalized amplitudes of PPG pulses, PPG pulse maximum slope, a location of the PPG pulse maximum slope, PPG pulse maximum curvature, or a location of the PPG pulse maximum curvature.

6. The method of claim 1, wherein the oxygen saturation prediction model comprises a neural network algorithm trained via machine learning over training data that includes one or more of: sets of blood oxygen level of a population of patients, sets of blood pressure values of the population of patients, or metrics derived from sets of PPG signals of the population of patients.

7. The method of claim 6, further comprising:

retraining the neural network algorithm to minimize incorrect predictions made using the oxygen saturation prediction model of oxygen saturation levels of the patient that miss deep oxygen desaturation events experienced by the patient.

8. The method of claim 1, further comprising:

determining, by the processing circuitry, offsets between oxygen saturation levels predicted using the oxygen saturation prediction model and actual oxygen saturation levels of the patient; and calibrating, by the processing circuitry, the oxygen saturation prediction model based at least in part on the determined offsets.

9. The method of claim 1, further comprising:

determining, by the processing circuitry and at the end of the predefined time period, whether the oxygen saturation level of the patient is above the desaturation threshold; and in response to determining that the oxygen saturation level of the patient is not above the desaturation threshold, outputting, by the processing circuitry, the indication of the patient experiencing the oxygen desaturation event.

10. The method of claim 1, wherein predicting, using the oxygen saturation prediction model, whether the oxygen saturation level of the patient will increase above the desaturation threshold by the end of the predefined time period further comprises:

determining, by the processing circuitry and using a plurality of oxygen saturation prediction models, a plurality of predictions of whether the oxygen saturation level of the patient will increase above the desaturation threshold by the end of the predefined time period; and predicting, by the processing circuitry and based at least in part on the plurality of predictions, whether the oxygen saturation level of the patient will increase above the desaturation threshold by the end of the predefined time period.

11. The method of claim 10, wherein the plurality of oxygen saturation prediction models comprise a plurality of neural network algorithms trained via machine learning.

12. The method of claim 10, wherein predicting, based at least in part on the plurality of predictions, whether the oxygen saturation level of the patient will increase above the desaturation threshold by the end of the predefined time period further comprises:

determining, by the processing circuitry, an average predicted oxygen saturation level by the end of the predefined time period from two or more of the plurality of predictions; and predicting, by the processing circuitry and based at least in part on the average predicted oxygen saturation level by the end of the predefined time period, whether the oxygen saturation level of the patient will increase above the desaturation threshold by the end of the predefined time period.

13. The method of claim 12, wherein determining the average predicted oxygen saturation level by the end of the predefined time period from the two or more of the plurality of predictions further comprises:

determining, by the processing circuitry, a weighted average predicted oxygen saturation level by the end of the predefined time period from the two or more of the plurality of predictions, wherein predicting whether the oxygen saturation level of the patient will increase above the desaturation threshold by the end of the predefined time period further comprises predicting, by the processing circuitry and based at least in part on the weighted average predicted oxygen saturation level, whether the oxygen saturation level of the patient will increase above the desaturation threshold by the end of the predefined time period.

14. The method of claim 12, wherein determining the average predicted oxygen saturation level by the end of the predefined time period from the two or more of the plurality of predictions further comprises:

adding, by the processing circuitry, a bias to the average predicted oxygen saturation level to determine a biased average predicted oxygen saturation level, wherein predicting whether the oxygen saturation level of the patient will increase above the desaturation threshold by the end of the predefined time period further comprises predicting, by the processing circuitry and based at least in part on the biased average predicted oxygen saturation level, whether the oxygen saturation level of the patient will increase above the desaturation threshold by the end of the predefined time period.

15. The method of claim 12, further comprising:

selecting, by the processing circuitry, the two or more of the plurality of predictions based at least in part on the two or more of the plurality of predictions being within a specified percentile of the plurality of predictions.

16. The method of claim 12, further comprising:
determining, by the processing circuitry, one or more outlier predictions from the plurality of predictions; and
refraining, by the processing circuitry, from including the one or more outlier predictions in the two or more of the plurality of predictions.

17. A system comprising:
an oxygen saturation sensing device configured to sense an oxygen saturation level of a patient; and
processing circuitry configured to:
receive a signal indicative of the oxygen saturation level of the patient;
determining, by the processing circuitry, that the signal indicates the oxygen saturation level is at or below a desaturation threshold;
in response to determining the oxygen saturation level of the patient is at or below the desaturation threshold, predict, using an oxygen saturation prediction model, whether the oxygen saturation level of the patient will increase above the desaturation threshold by the end of a predefined time period; and
in response to predicting that the oxygen saturation level of the patient will increase above the desaturation threshold by the end of the predefined time period, refrain from outputting an indication of the patient experiencing an oxygen desaturation event.

18. The system of claim 17, wherein the processing circuitry is further configured to:
in response to predicting that the oxygen saturation level of the patient will increase above the desaturation threshold by the end of the predefined time period, determine, prior to the end of the predefined time period, whether the oxygen saturation level of the patient has decreased below a deep desaturation threshold; and
in response to determining that the oxygen saturation level of the patient has decreased below the deep desaturation threshold, output an indication of the patient experiencing a deep oxygen desaturation event.

19. The system of claim 17, wherein the processing circuitry is further configured to:
in response to predicting that the oxygen saturation level of the patient will increase above the desaturation threshold within the predefined time period, determine, prior to the predefined time period ending, whether the oxygen saturation level of the patient is continuing to decrease; and
in response to determining that the oxygen saturation level of the patient is continuing to decrease, outputting the indication of the patient experiencing the oxygen desaturation event.

20. The system of claim 17, wherein to predict, using the oxygen saturation prediction model, whether the oxygen saturation level of the patient will increase above the desaturation threshold within the predefined time period, the processing circuitry is further configured to:
inputting one or more of: a history of oxygen saturation levels of the patient over a time period immediately prior to the oxygen saturation level of the patient being at or below the desaturation threshold, a history of blood pressure values of the patient over the time period, or one or more metrics derived from photoplethysmographic (PPG) signals of the patient over the time period into the oxygen saturation prediction model to predict whether the oxygen saturation level of the patient will increase above the desaturation threshold within the predefined time period.

21. The system of claim 20, wherein the one or more metrics derived from the PPG signals of the patient comprises one or more of: PPG pulse skews, PPG pulse amplitudes, normalized amplitudes of PPG pulses, PPG pulse maximum slope, a location of the PPG pulse maximum slope, PPG pulse maximum curvature, or a location of the PPG pulse maximum curvature.

22. The system of claim 17, wherein the oxygen saturation prediction model comprises a neural network algorithm trained via machine learning over training data that includes one or more of: sets of blood oxygen level of a population of patients, sets of blood pressure values of the population of patients, or metrics derived from sets of PPG signals of the population of patients.

23. The system of claim 22, wherein the processing circuitry is further configured to:
retrain the neural network algorithm to minimize incorrect predictions made using the oxygen saturation prediction model of oxygen saturation levels of the patient that miss deep oxygen desaturation events experienced by the patient.

24. The system of claim 17, wherein the processing circuitry is further configured to:
determine offsets between oxygen saturation levels predicted using the oxygen saturation prediction model and actual oxygen saturation levels of the patient; and
calibrate the oxygen saturation prediction model based at least in part on the determined offsets.

25. The system of claim 17, wherein the processing circuitry is further configured to:
determine, at the end of the predefined time period, whether the oxygen saturation level of the patient is above the desaturation threshold; and
in response to determining that the oxygen saturation level of the patient is not above the desaturation threshold, output the indication of the patient experiencing the oxygen desaturation event.

26. The system of claim 17, wherein to predict, using the oxygen saturation prediction model, whether the oxygen saturation level of the patient will increase above the desaturation threshold by the end of the predefined time period, the processing circuitry is further configured to:
determine, using a plurality of oxygen saturation prediction models, a plurality of predictions of whether the oxygen saturation level of the patient will increase above the desaturation threshold by the end of the predefined time period; and
predict, based at least in part on the plurality of predictions, whether the oxygen saturation level of the patient will increase above the desaturation threshold by the end of the predefined time period.

27. The system of claim 26, wherein the plurality of oxygen saturation prediction models comprise a plurality of neural network algorithms trained via machine learning.

28. The system of claim 26, wherein to predict, based at least in part on the plurality of predictions, whether the oxygen saturation level of the patient will increase above the desaturation threshold by the end of the predefined time period, the processing circuitry is further configured to:
determine an average predicted oxygen saturation level by the end of the predefined time period from two or more of the plurality of predictions; and
predict, based at least in part on the average predicted oxygen saturation level by the end of the predefined time period, whether the oxygen saturation level of the patient will increase above the desaturation threshold by the end of the predefined time period.

29. The system of claim 28, wherein to determine the average predicted oxygen saturation level by the end of the predefined time period from the two or more of the plurality of predictions, the processing circuitry is further configured to:
- determine a weighted average predicted oxygen saturation level by the end of the predefined time period from the two or more of the plurality of predictions,
- wherein to predict whether the oxygen saturation level of the patient will increase above the desaturation threshold by the end of the predefined time period, the processing circuitry is further configured to predict, based at least in part on the weighted average predicted oxygen saturation level, whether the oxygen saturation level of the patient will increase above the desaturation threshold by the end of the predefined time period.

30. The system of claim 28, wherein to determine the average predicted oxygen saturation level by the end of the predefined time period from the two or more of the plurality of predictions, the processing circuitry is further configured to:
- add a bias to the average predicted oxygen saturation level to determine a biased average predicted oxygen saturation level; and
- wherein to predict whether the oxygen saturation level of the patient will increase above the desaturation threshold by the end of the predefined time period, the processing circuitry is further configured to predict, based at least in part on the biased average predicted oxygen saturation level, whether the oxygen saturation level of the patient will increase above the desaturation threshold by the end of the predefined time period.

31. The system of claim 28, wherein the processing circuitry is further configured to:
- select the two or more of the plurality of predictions based at least in part on the two or more of the plurality of predictions being within a specified percentile of the plurality of predictions.

32. The system of claim 28, wherein the processing circuitry is further configured to:
- determine one or more outlier predictions from the plurality of predictions; and
- refrain from including the one or more outlier predictions in the two or more of the plurality of predictions.

33. A non-transitory computer readable storable medium comprising instructions that, when executed, cause processing circuitry to:
- receive a signal indicative of an oxygen saturation level of a patient;
- determining, by the processing circuitry, that the signal indicates the oxygen saturation level is at or below a desaturation threshold;
- in response to determining the oxygen saturation level of the patient is at or below the desaturation threshold, predict, using an oxygen saturation prediction model, whether the oxygen saturation level of the patient will increase above the desaturation threshold by the end of a predefined time period; and
- in response to predicting that the oxygen saturation level of the patient will increase above the desaturation threshold by the end of the predefined time period, refrain from outputting an indication of the patient experiencing an oxygen desaturation event.

* * * * *